US008628238B2

(12) United States Patent
Fesmire et al.

(10) Patent No.: US 8,628,238 B2
(45) Date of Patent: Jan. 14, 2014

(54) INSULATION TEST CRYOSTAT WITH LIFT MECHANISM

(75) Inventors: James E. Fesmire, Titusville, FL (US); Adam G. Dokos, Titusville, FL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 600 days.

(21) Appl. No.: 12/813,864

(22) Filed: Jun. 11, 2010

(65) Prior Publication Data

US 2010/0318316 A1    Dec. 16, 2010

Related U.S. Application Data

(60) Provisional application No. 61/186,475, filed on Jun. 12, 2009.

(51) Int. Cl.
*G01N 25/18* (2006.01)

(52) U.S. Cl.
USPC ................ 374/44; 374/45; 374/141; 374/147

(58) Field of Classification Search
USPC ............................... 422/51; 74/174, 383, 640
See application file for complete search history.

(56) References Cited

U.S. PATENT DOCUMENTS

| | | | | | |
|---|---|---|---|---|---|
| 2,995,330 | A | * | 8/1961 | Alms ............................ | 248/145 |
| 3,782,128 | A | * | 1/1974 | Hampton et al. .............. | 62/45.1 |
| 4,084,706 | A | * | 4/1978 | Russell .......................... | 414/460 |
| 4,350,017 | A | * | 9/1982 | Kneip et al. .................... | 62/48.1 |
| 5,339,650 | A | * | 8/1994 | Hakamada et al. ............ | 62/51.1 |
| 5,758,785 | A | * | 6/1998 | Spinosa et al. ................ | 212/300 |
| 6,487,866 | B1 | * | 12/2002 | Fesmire et al. ................ | 62/51.1 |
| 6,742,926 | B1 | * | 6/2004 | Fesmire et al. ................. | 374/45 |
| 6,824,306 | B1 | | 11/2004 | Fesmire | |
| 7,540,656 | B1 | * | 6/2009 | Stochl et al. .................... | 374/29 |
| 2007/0220904 | A1 | * | 9/2007 | Jibb et al. ....................... | 62/50.7 |
| 2009/0092170 | A1 | * | 4/2009 | Brushwyler et al. ........... | 374/33 |

OTHER PUBLICATIONS

Swagelok. (Nov. 2002) "Bellows-Sealed Valves". Retrieved from: http://hepunx.rl.ac.uk/BFROOT/www/Detector/IFR/llnl/gasmixer/hardware/shutoff_valves1.pdf.*

(Continued)

*Primary Examiner* — Lisa Caputo
*Assistant Examiner* — Janice M Soto
(74) *Attorney, Agent, or Firm* — Michelle L. Ford; David E. Franklin

(57) ABSTRACT

A multi-purpose, cylindrical thermal insulation test apparatus is used for testing insulation materials and systems of materials using a liquid boil-off calorimeter system for absolute measurement of the effective thermal conductivity (k-value) and heat flux of a specimen material at a fixed environmental condition (cold-side temperature, warm-side temperature, vacuum pressure level, and residual gas composition). The apparatus includes an inner vessel for receiving a liquid with a normal boiling point below ambient temperature, such as liquid nitrogen, enclosed within a vacuum chamber. A cold mass assembly, including the upper and lower guard chambers and a middle test vessel, is suspended from a lid of the vacuum canister. Each of the three chambers is filled and vented through a single feedthrough. All fluid and instrumentation feedthroughs are mounted and suspended from a top domed lid to allow easy removal of the cold mass. A lift mechanism allows manipulation of the cold mass assembly and insulation test article.

29 Claims, 17 Drawing Sheets

(56) References Cited

OTHER PUBLICATIONS

Scholtens, et al., "Cryogenic Thermal Performance Testing of Bulk-Fill and Aerogel Insulation Materials," Advances in Cryogenic Engineering: Transactions of the Cryogenic Engineering Conference—CEC, vol. 52. AIP Conference Proceedings, vol. 985, pp. 152-159 (2008).

Fesmire, et al., "Thermal Performance Testing of Cryogenic Insulation Systems," International Thermal Conductivity Conference 29, Birmingham, AL USA Jun. 2007.

Fesmire, et al., "Equipment and Methods for Cryogenic Thermal Insulation Testing," Advances in Cryogenic Engeineering: Transactions of the Cryogenic Engineering Conference—CEC. AIP Conference Proceedings, vol. 710, pp. 579-586 (2004).

Fesmire and Augustynowicz, "Insulation Testing Using Cryostat Apparatus With Sleeve," Advances in Cryogenic Engineering (2000), 45 1683-1690.

* cited by examiner

| | A | B | C | D | E | F | G | H |
|---|---|---|---|---|---|---|---|---|
| 2 | Cryostat-100 | | | | | | | |
| 4 | Calculate heat flux and apparent thermal conductivity | | | | | | | |
| 6 | Input Data | | | | | | | |
| 7 | h | heat of vaporization at Psat | J/g | Input: | 198.6 | | | |
| 8 | m | boil-off rate | g/sec | Formula=(G8*E17)/60: | 0.001 | Input: | 55 | sccm |
| 9 | L | cold mass effective length | m | Formula=G9*0.0254: | 0.580 | Input: | 22.82 | inch |
| 10 | k | apparent thermal conductivity | mW/m-K | | | | | |
| 11 | WBT | Warm Boundary Temperature | K | Input: | 300 | | | |
| 12 | CBT | Cold Boundary Temperature | K | Input: | 78 | | | |
| 13 | D | cold mass diameter | m | Formula=G13*0.0254: | 0.167 | Input: | 6.58 | inch |
| 14 | Do | insulation outside diameter | m | Formula=G14*0.0254: | 0.201 | Input: | 7.90 | inch |
| 15 | Di | sleeve outside diameter | m | Formula=G15*0.0254: | 0.167 | Input: | 6.58 | inch |
| 16 | DX | insulation thickness | m | Formula=($E$14-$E$13)/2: | 0.017 | Formula=E16 *1000: | 16.764 | mm |
| 17 | r_gas | density of gas at: 0oC and 101.3 kPa | g/cm3 | Input: | 0.00125 | | | |
| 18 | r_liq | density of liquid at Psat = 0.1 PSIG | g/cm3 | Input: | 0.80 | | | |
| 19 | Ao | insulation outside area | m2 | Formula=3.1416*$E$14*$E$9 : | 0.365 | | | |
| 20 | Ai | insulation inside area | m2 | Formula=3.1416*$E$15*$E$9 : | 0.304 | | | |

FIG. 8

INSULATION TEST CRYOSTAT WITH LIFT MECHANISM

CROSS-REFERENCE TO RELATED APPLICATIONS

This application claims the benefit of priority under 35 U.S.C. §119(e) to U.S. Provisional Application Ser. No. 61/186,475 entitled "INSULATION TEST CRYOSTAT INCLUDING LIFT MECHANISM," filed Jun. 12, 2009, the contents of which are incorporated herein by reference.

ORIGIN OF INVENTION

The invention described herein was made by employees of the United States Government and may be manufactured and used by or for the Government of the United States of America for governmental purposes without the payment of any royalties thereon or therefore.

BACKGROUND OF THE INVENTION

1. Field

The present disclosure relates generally to testing of material to determine thermal conductivity of a material or system of materials.

2. Background

In today's world of increasing demands for energy and energy efficiency, the use of cryogenics and refrigeration is taking on a more and more significant role. From the food industry, transportation, energy, and medical applications to the Space Shuttle, cryogenic liquids and other refrigerants must be stored, handled, and transferred from one point to another without losing their unique properties. To protect storage tanks, transfer lines, and other process system equipment from heat energy, high-performance materials are needed to provide effective thermal insulation to a degree that can be reasonably obtained. Complete and accurate thermal characterization of the insulation material, i.e., performance attributes of the material such as thermal conductivity and heat flux, is a key aspect in designing efficient and effective low-maintenance cryogenic and low-temperature systems.

One valuable technique for testing the thermal performance of materials, such as insulation material, is evaporation or boil-off testing. Boil-off testing is accomplished by filling a vessel with a fluid which evaporates or boils below ambient temperature. In the general sense, boiling is associated with higher heat transfer rates and evaporation with lower heat transfer rates. Although the exemplary fluid is the cryogen liquid nitrogen, other fluids such as liquid helium, liquid methane, liquid hydrogen, or known refrigerants may be used. A vessel is surrounded with the testing material, placed in a suitable environmental chamber, and then filled with the test fluid such as a cryogenic liquid. A calorimetry method is then used to determine the thermal conductivity of the test material by first determining the rate of heat passing through the test material to the vessel containing the refrigerant liquid. The heat leakage rate passing through the test material to the liquid in the vessel is directly proportional to the liquid boil-off rate from the vessel. For a test material under a set vacuum pressure, the effective thermal conductivity (k-value) and/or heat flux is determined by measuring the flow rate of boil-off at prescribed warm and cold boundary temperatures across the thickness of the sample.

Although other cryogenic boil-off techniques and devices have been prepared to determine the thermal conductivity of insulation material, the previous techniques and devices are undesirable for a variety of reasons. First, few such cryogenic devices are in operation because of their impracticality from an engineering point of view. The previous boil-off devices made it extremely difficult to obtain accurate, stable measurements and required extremely long set up times. Prior testing devices also needed highly skilled personnel that could oversee the operation of the testing device for extended periods of time, over 24 hours to many days in some cases. Additionally, constant attention was required to operate previous testing devices to make the necessary fine adjustments required of the testing apparatus. Second, prior testing devices contained the limitation that they did not permit the testing of continuously rolled products which are commonly used insulation materials. The testing of high-performance materials such as multilayer insulation requires extreme care in fabrication and installation. Inconsistency in wrapping techniques is a dominant source of error and poses a basic problem in the comparison of such materials. Improper treatment of the ends or seams can render a measurement several times worse than predicted. Localized compression effects, sensor installation, and outgassing are further complications. Third, measurements of various testing parameters were not carefully determined or controlled in previous testing devices. Measurement of temperature profiles for insulation material was either not done or was minimal because of the practical difficulties associated with the placement, feed-through, and calibration of the temperature sensors. Vacuum levels were restricted to one or two set points or not actively controlled altogether. Fourth, previous cryogenic testing devices required complex thermal guards having cryogenic fluid-filled chambers to reduce unwanted heat leaks (end effects) to a tolerable level. The previous technique for providing thermal guards, filling guard chambers with the cryogen, caused much complexity both in construction and operation of the apparatus. Known techniques add the further complication of heat transfer between the test chamber and the guard chambers due to the thermal stratification and destratification processes of the liquid within the chambers.

SUMMARY OF THE INVENTION

The following presents a simplified summary in order to provide a basic understanding of some aspects of the disclosed invention. This summary is not an extensive overview and is intended to neither identify key or critical elements nor delineate the scope of such aspects. Its purpose is to present some concepts of the described features in a simplified form as a prelude to the more detailed description that is presented later.

In accordance with one or more embodiments and corresponding disclosure thereof, various aspects are described in connection with boil-off calorimetric measuring of an absolute thermal conductivity.

In one embodiment, an apparatus adaptable for use with a boil-off flow measuring device is provided for determining thermal performance of a testing material. A cold mass comprises an inner vessel having a top, a bottom, a sidewall defining a testing chamber, the sidewall for receiving a testing material, an upper guard chamber positioned at the top of the inner vessel, and a lower guard chamber positioned at the bottom of the inner vessel. An outer vacuum chamber encloses the inner vessel and the testing material. A plurality of liquid conduits receives a cryogenic fluid having a normal boiling point below ambient temperature and for venting cryogenic gas. Each of the plurality of liquid conduits communicates through the outer vacuum chamber to a respective one of the testing chamber, the upper guard chamber, and the lower guard chamber.

In another embodiment, a method is provided for testing thermal conductivity or heat flux. A cylindrical test specimen is positioned around a cylindrical cold mass comprised of a stacked upper vessel, top thermal guard, test vessel, a bottom thermal guard, and a lower vessel, which in turn is within a vacuum chamber. Each of the stacked upper vessel, test vessel, and lower vessel of the cylindrical cold mass are filled and vented with a cryogenic liquid via a respective top fed feedthrough. A cold vacuum pressure is maintained within the vacuum chamber. A cold boundary temperature of an inner portion of the test specimen and a warm boundary temperature of an outer portion of the test specimen is measured while the cryogenic fluid maintains a set temperature of the cold mass. An effective thermal conductivity is calculated for the test specimen based upon the cryogenic fluid boil-off or evaporation flow rate cold boundary temperature, warm boundary temperature, effective heat transfer surface area of the cold mass, and thickness of the specimen.

In additional embodiment, an apparatus is provided for measuring thermal conductivity or heat flux. A vacuum canister has a lid attachable and sealable to a lower cylindrical portion. A cold mass comprises a vertical cylindrical stack of an upper vessel, a test vessel, and a lower vessel. Three feedthrough conduits pass through the lid of the vacuum canister respectively to fill and to vent respectively one of the upper vessel, test vessel, and lower vessel. A vertical machine jack screw positions a carriage engagable to the lid of the vacuum canister for positioning the cold mass suspended from the lid into the lower cylindrical portion. A vacuum system produces and measures either a warm vacuum pressure or a cold vacuum pressure within the vacuum canister. A boil-off calorimeter measuring system determines boil-off flow rate coincident with a stable thermal environment of a test specimen positioned around the cold mass.

To the accomplishment of the foregoing and related ends, one or more embodiments comprise the features hereinafter fully described and particularly pointed out in the claims. The following description and the annexed drawings set forth in detail certain illustrative embodiments and are indicative of but a few of the various ways in which the principles of the embodiments may be employed. Other advantages and novel features will become effective from the following detailed description when considered in conjunction with the drawings and the disclosed embodiments, which are intended to include all such aspects and their equivalents.

BRIEF DESCRIPTION OF THE DRAWINGS

The features, nature, and advantages of the present invention as described in this specification will become more effective from the detailed description set forth below when taken in conjunction with the drawings in which like reference characters identify correspondingly throughout and wherein:

FIG. 8 illustrates a screen depiction of a methodology utilizing a spreadsheet for calculating mean heat transfer rate and k-value for concentric cylindrical geometry.

DETAILED DESCRIPTION OF THE INVENTION

Figure 1:
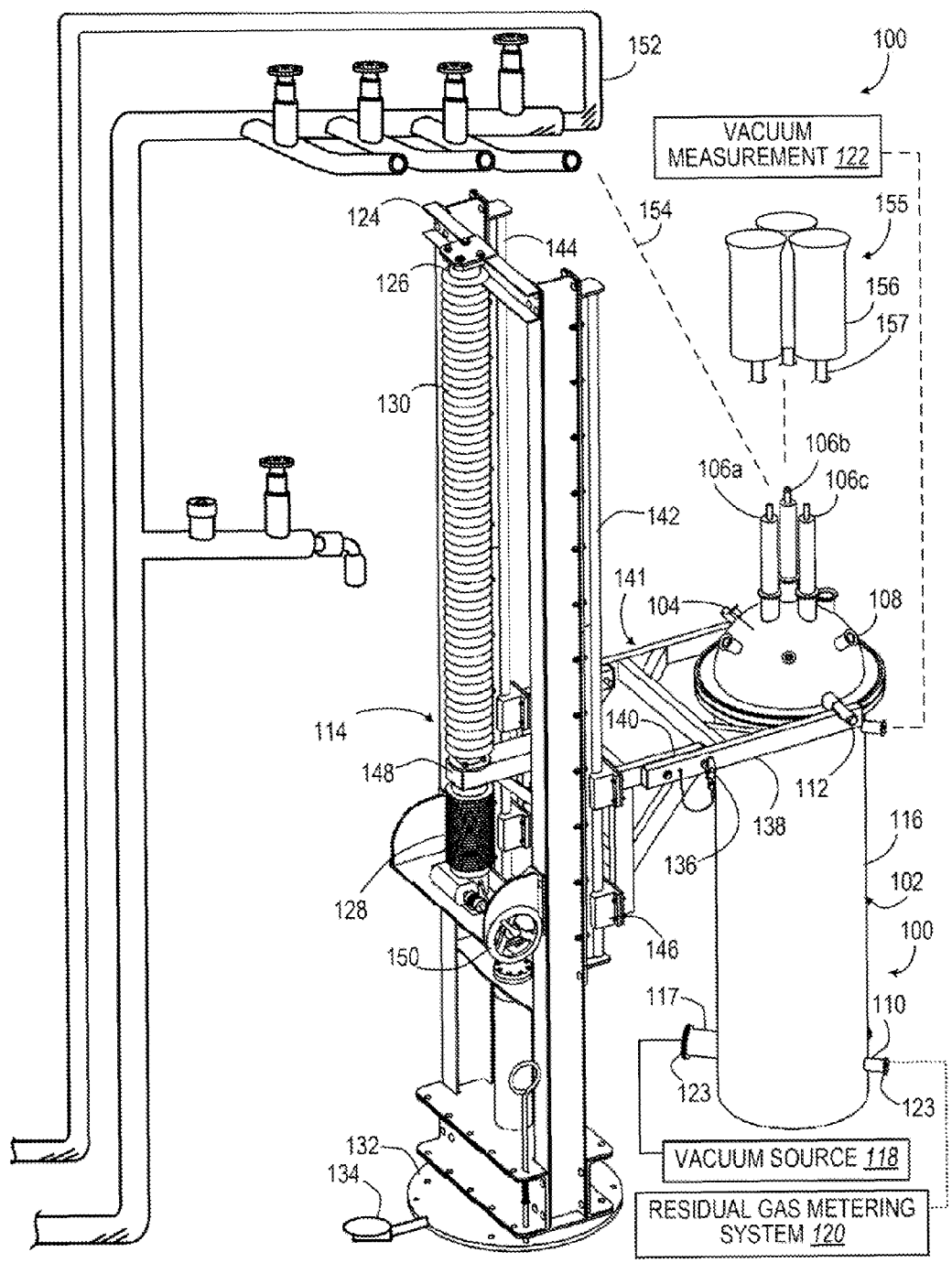
FIG. 1 illustrates an isometric view of a cryogenic testing apparatus supported by a lifting mechanism with a schematic view of a boil-off calorimeter system for absolute measurement of effective thermal conductivity (k-value).

A multi-purpose, cylindrical thermal insulation test apparatus is used for testing insulation materials and systems of materials using a fluid boil-off calorimeter system for absolute measurement of the effective thermal conductivity (k-value) and heat flux of a specimen material at a fixed environmental condition (or vacuum pressure level). The apparatus includes an inner vessel for receiving a fluid with a normal boiling point below ambient temperature, such as liquid nitrogen, enclosed within a vacuum chamber. A cold mass assembly, including the upper and lower guard chambers and a middle test vessel, is suspended from a lid of the vacuum canister. Each of the three chambers is filled and vented through a single low conductivity feedthrough. All fluid and instrumentation feedthroughs are mounted in the top domed lid to allow easy removal of the cold mass. A lift mechanism is attached to the top lid of the vacuum can to allow removal of the cold mass assembly and convenient manipulation of the assembly for the installation, wrapping, or placement of insulation test materials around the outer cylindrical surface of the cold mass. The k-value of the insulation material is calculated based upon the cryogen boil-off (or evaporation) flow rate cold boundary temperature, warm boundary temperature, effective heat transfer surface area of the cold mass, and thickness of the specimen. Similarly, the mean heat flux for the test specimen is based upon the cryogen boil-off (or evaporation) flow rate, effective heat transfer surface area of the cold mass, and thickness of the specimen.

The evaluation of cryogenic thermal insulation materials and systems is a technology focus area of the Cryogenics Test Laboratory at NASA Kennedy Space Center. To that end, new test procedures and devices have been established to test insulation materials under the combination of full temperature difference and full-range vacuum conditions. The Cryostat-1 apparatus performs absolute/cylindrical testing, while the Cryostat-2 apparatus achieves comparative/cylindrical testing and the Cryostat-4 apparatus performs comparative/flat disk testing. The different methods are considered to be naturally complementary. No one type of test will provide all the heat transfer information needed. No one type of test will be readily suited for all different types and forms of materials and combinations of materials. As will be explained in greater detail, the present invention (hereinafter "device" or "Cryostat-100") combines and improves the best attributes of existing apparatuses to create a unique device capable of providing practical, scientific data for real-world insulation systems that can readily be applied to a myriad of design engineering problems or operational issues.

The present invention comprises an apparatus that requires significantly less ancillary equipment to operate properly (e.g., not connected to storage tank, phase separator, subcooler, etc.). The device is top loading for convenience of use and, more importantly, exhibits much improved thermal stability due to internal vapor plates, a single-tube system of filling and venting, bellows feedthroughs, stainless steel wire or polymer fiber, such as aromatic polyamide fiber (known as KEVLAR), thread suspensions, and thick-wall stainless steel construction. The device can readily do the full range of cryogenic-vacuum condition testing over several orders of magnitude of heat flux. Guide rings, handling tools, and other design improvements make insulation specimen change out and test measurement verification highly reliable and efficient to operate.

In particular, a very wide heat flux (or k-value) capability of approximately four orders of magnitude is enabled by many design factors to include the following:

The dimensions (length to diameter and relationship of all 3 chambers) of the cold mass are such that stratification of the cryogen sets-up in the right amount of time;

These dimensions are also such that the heat transfer rates, boil-off flow rates, and resulting changes in liquid levels are approximately the same in a given test;

The vapor generation and resulting convection current from the boiling or evaporation of the cryogen is routed straight away from the liquid surface in each chamber; and The top and bottom edges of the cold mass are thermally guarded by a combination system of multilayer insulation (such as 60 layers aluminum foil and micro-fiberglass paper), vacuum-quality micro-fiberglass blanket, aerogel blanket, and aerogel bulk-fill materials as required.

Thus, unlike a conventionally known approach, the Cryostat-100 apparatus does not require a large LN2 storage tank, sub cooler unit, an adjustable phase separator tank, or "keep full" devices along vacuum jacketed pipes. It should be appreciated a benefit of the present invention is that it has half the internal plumbing of the conventional approach, is more efficient, is cost effective, and safer (e.g., less cryogenic supply infrastructure and thus less inherent risk). The Cryostat-100 apparatus is truly designed for the entire vacuum pressure range from $1 \times 10^{-6}$ torr to 1000 torr (i.e., a torr is $1/760^{th}$ of an atmosphere).

This invention (Cryostat-100) follows and builds upon these three patents, which are hereby incorporated by reference in their entirety:

(1) "Thermal Insulation Testing Method and Apparatus," U.S. Pat. No. 6,824,306 issued Nov. 30, 2004 (Cryostat-1);

(2) "Methods of Testing Thermal Insulation and Associated Test Apparatus," U.S. Pat. No. 6,742,926 issued Jun. 1, 2004 (Cryostat-4); and (3) "Multi-purpose Thermal Insulation Test Apparatus," U.S. Pat. No. 6,487,866 issued Dec. 3, 2002 (Cryostat-2). Cryostat-100 is an improvement and replacement for Cryostat-1, incorporating features from both Cryostat-2 and Cryostat-4 and providing additional innovations.

In one embodiment, a method is provided that is adaptable for use with a boil-off flow measuring device for determining thermal performance of a testing material. A cold mass comprises an inner vessel having a top, a bottom, a sidewall defining a testing chamber, and the sidewall for receiving a testing material. The cold mass also comprises a first thermal guard chamber positioned at the top of the inner vessel and a second thermal guard chamber positioned at the bottom of the inner vessel. An outer vacuum chamber encloses the inner vessel and the testing material. A plurality of liquid conduits receives a cryogenic fluid having a normal boiling point below ambient temperature. Each liquid conduit communicates through the outer vacuum chamber to a respective one of the testing chamber, first thermal guard chamber, and second thermal guard chamber.

In another embodiment, a method is provided for testing thermal conductivity. A cylindrical test specimen is positioned around a cylindrical cold mass comprised of a stacked upper vessel, test vessel, and lower vessel, which in turn is within a vacuum chamber. Each of the stacked upper vessel, test vessel, and lower vessel of the cylindrical cold mass are filled and vented via a respective top feedthrough. Both the filling and the venting process are achieved through a single port for each chamber. A filling tube with certain hole patterns at the lower end connected to a top funnel is used to accomplish the cool down and filling of a given chamber. The single port method greatly simplifies the overall complexity of the apparatus and reduces the solid conduction heat leak from the vacuum can to the cold mass by about half (compared to prior method of separate ports for filling and venting). A cold vacuum pressure is maintained within the vacuum chamber. This vacuum level can be automatically maintained at any pressure desired using a gaseous feed controller connected to a suitable pressure transducer. A cold boundary temperature of an outer portion of the test specimen and a warm boundary temperature of an inner portion of the test specimen are measured while maintaining a set temperature of the cold mass (by virtue of the full or essentially full cold mass). The warm boundary temperature is maintained by a combination of electrical heaters. A system of heater elements mounted on a sleeve mounted inside the vacuum chamber wall provides fine warm boundary control. A heater jacket on the externals of the vacuum can provides overall heat control and system bake-out capability. An effective thermal conductivity for the test specimen at a given cold vacuum pressure is calculated based upon the boil-off flow rate, cold boundary temperature, warm boundary temperature, and inside and outside diameter of the specimen (thickness).

In an exemplary embodiment, the heating of the outer surface of the insulation test article is a critical part of the operation for producing steady-state conditions. The design includes bake-out heaters on the outside of the vacuum can for rough level of heating control. The design includes a custom heating system on the inside of the vacuum can that includes a high emissivity black coated aluminum sleeve with a number of thin film heaters glued on with a special high-temperature, vacuum compatible adhesive; the heaters are wired together for a single point temperature control; thermocouples are attached to the sleeve to provide the reference temperature.

In an additional embodiment, an apparatus is provided for measuring thermal conductivity. A vacuum canister has a lid that is attachable and sealable to a lower cylindrical portion. A cold mass is comprised of a vertical cylindrical stack of an upper vessel, a test vessel, and a lower vessel. Three feedthrough conduits pass through the lid of the vacuum canister to fill and to vent, respectively, the upper vessel, the test vessel, and the lower vessel. A vertical machine jack screw positions a carriage engagable to the lid of the vacuum canister for positioning the cold mass suspended from the lid into the lower cylindrical portion. Alternatively, an overhead hoist can be used. A vacuum system and gaseous purge feed system together produce the desired vacuum pressure within the vacuum canister. The vacuum pressure level is measured by a number of transducers as desired. Typically, three different transducers are used to cover the entire range of measurement from high vacuum to ambient pressure. The warm boundary temperature is measured by a plurality of temperature sensors such as thermocouples. Intermediate temperatures may also be similarly measured to allow the calculation of layer-by-layer thermal conductivity through the thickness of a specimen. The cold boundary temperature of a test specimen positioned around the cold mass is measured by temperature sensors placed on the cold mass surface or may be accurately determined by the saturation temperature of the liquid in correspondence to the prevailing atmospheric pressure (room pressure). The inner diameter of the cold mass is known and the outer diameter of the insulation specimen is taken by circumference measurement or other suitable means.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form in order to facilitate describing these embodiments.

In FIG. 1, to eliminate or minimize the foregoing and other problems, a new method of testing cryogen insulation systems has been developed. In particular, the present invention overcomes the foregoing problems by providing a cryogenic testing (Cryostat-100) apparatus 100 having a boil-off calorimeter system for calibrated measurement of the effective thermal conductivity (k-value) of a testing material (not shown in FIG. 1), for example insulation material, at a fixed vacuum level.

It should be appreciated with benefit of the present disclosure that the Cryostat-100 apparatus 100 is an absolute instrument meaning that what you get (boil-off) is directly proportional to what you want (thermal conductivity or heat flux), with no calibration required. Boil-off flow is directly proportional to the heat energy rate (power) through the thickness of the test specimen and no calibration is required. By contrast, some means of suitable calibration is appropriate for any tester that is not absolute and also any absolute tester that measures heat indirectly, such as by electrical power balances. In fact, the Cryostat-100 apparatus 100 meets a need to calibrate measurement devices that are comparative type or indirect type.

In particular, a vacuum canister 102 has a lid 104 with three feedthroughs 106a-106c capable of filling and venting a cryogenic fluid (e.g., liquid nitrogen (LN2)), a view port 108, auxiliary ports 110 for instrumentation, and a pair of lifting supports (handling lugs) 112. A uniquely designed lift mechanism 114 can be utilized to perform rapid and efficient change out of insulation test specimen from the Cryostat-100 apparatus 100. The lifting mechanism 114 raises and lowers the lid 104 in order to mount and seal to a lower cylindrical portion 116 to the lid 104. The lower cylindrical portion 116 has a flange vacuum port 117 for connecting to a vacuum source 118 and auxiliary ports 110, such as for connecting to a residual gas metering system 120 and for connecting to a vacuum measurement sensor 122. The vacuum pumping (evacuation) and gaseous back-filling processes are very important to all types of cryostat testing. The design includes baffles 123 at the main vacuum pumping ports on the bottom (not shown in FIG. 1).

The lift mechanism 114 has a frame 124 whose top bearing support 126 and lower bellows 128 receives for rotation a machine screw jack 130 that is vertically aligned. The frame 124 is supported by a locking turntable 132 that can be selectively released by a turntable release pedal 134 for rotation left or right for readily facilitating working on and changing out the cold mass assembly (described below). Ball lock pins 136 horizontally lock respectively a breakaway lift arms assembly 138 to an elevator frame 140 to form a carriage 141 received for vertical movement on the frame 124. The breakaway lift arms assembly 138 has distal ends that receive the lifting supports (handling lugs) 112 of the vacuum canister 102 and has proximal ends that are pivotally attached to the elevator frame 140.

The frame 124 has a pair of vertically aligned and parallel linear bearing rails 142, 144 that receive for vertical movement a plurality of pillow block bearings 146 of the carriage 141 and an actuator arm 148 that is thread engaged to the machine screw jack 130 for being raised or lowered as the machine screw jack 130 is rotated, which in an exemplary implementation is by a hand wheel 150 that has a hand drill adapter (not shown).

Liquid nitrogen (LN2) filling assembly 152 provides funnels and flexible hoses for connecting to the three feedthroughs 106a-106c as depicted at 154.

In an illustrative implementation, however, a portable 10-liter dewar (not shown) can be poured manually into funnel assemblies 155, each comprising a funnel 156 and a funnel tube 157. Note that the funnels 156 can be wrapped with aerogel blanket material and further wrapped with shrink wrap plastic film that hangs down a few inches below the bottom of the funnel 156 (not shown). These skirts keep the area around the feedthrough 106a-106c of the cryostat 100 apparatus 100 "purged" by the nitrogen coming out and therefore reducing moisture and ice formation which could cause blockage or a tube getting stuck.

It should be appreciated with the benefit of the present invention that the dimensions can be selected to be sufficient for the required rate of filling and venting using a single port for each chamber. Alternatively or in addition, multiple ports for each chamber can be sized in order to accommodate a larger thermal flux without necessarily changing the diameters of the tubing.

In an exemplary implementation, filling tubes 157 are 5/16" SST thin-wall tubing (0.030"). The thinner the wall thickness, the better to provide more flow area and less cool down mass. Since the tubes are long, sufficient strength is provided to avoid damage during handling. In one embodiment, tubing of 3/8" can be used, although the limited clearance to the inner diameter of the feedthrough 106a-106c can tend to get stuck or provide insufficient venting. In TABLE 1, exemplary dimensions are provided for 5/16" SST funnel tubes 157.

TABLE 1

| Length (inches) | Sets of holes* | Distance (inches) of each set of holes from the bottom | Hole Size (in) | Total # of holes |
|---|---|---|---|---|
| 32 | 4 | 0.5 | 5/32 | 16 |
| Top #1 | | 1.5 | 5/32 | |
| | | 7.5 | 1/12 | |
| | | 8 | 1/12 | |

TABLE 1-continued

| Length (inches) | Sets of holes* | Distance (inches) of each set of holes from the bottom | Hole Size (in) | Total # of holes |
|---|---|---|---|---|
| 55 Middle #2 | 6 | 0.5 | 5/32 | 24 |
| | | 1.5 | 5/32 | |
| | | 2.5 | 5/32 | |
| | | 3.5 | 5/32 | |
| | | 21.5 | 1/12 | |
| | | 22 | 1/12 | |
| 58.5 Bottom #3 | 2 | 0.5 | 5/32 | 8 |
| | | 1 | 1/12 | |

Each set of holes contains 4 holes. The holes in each set can be spaced 90° apart. The bottom of the tube can be rolled in slightly. The top of the tube can be flared to 3/8" flared tube fitting (37.5 degree KC or AN) to connect to the funnel 156.

Figure 2:
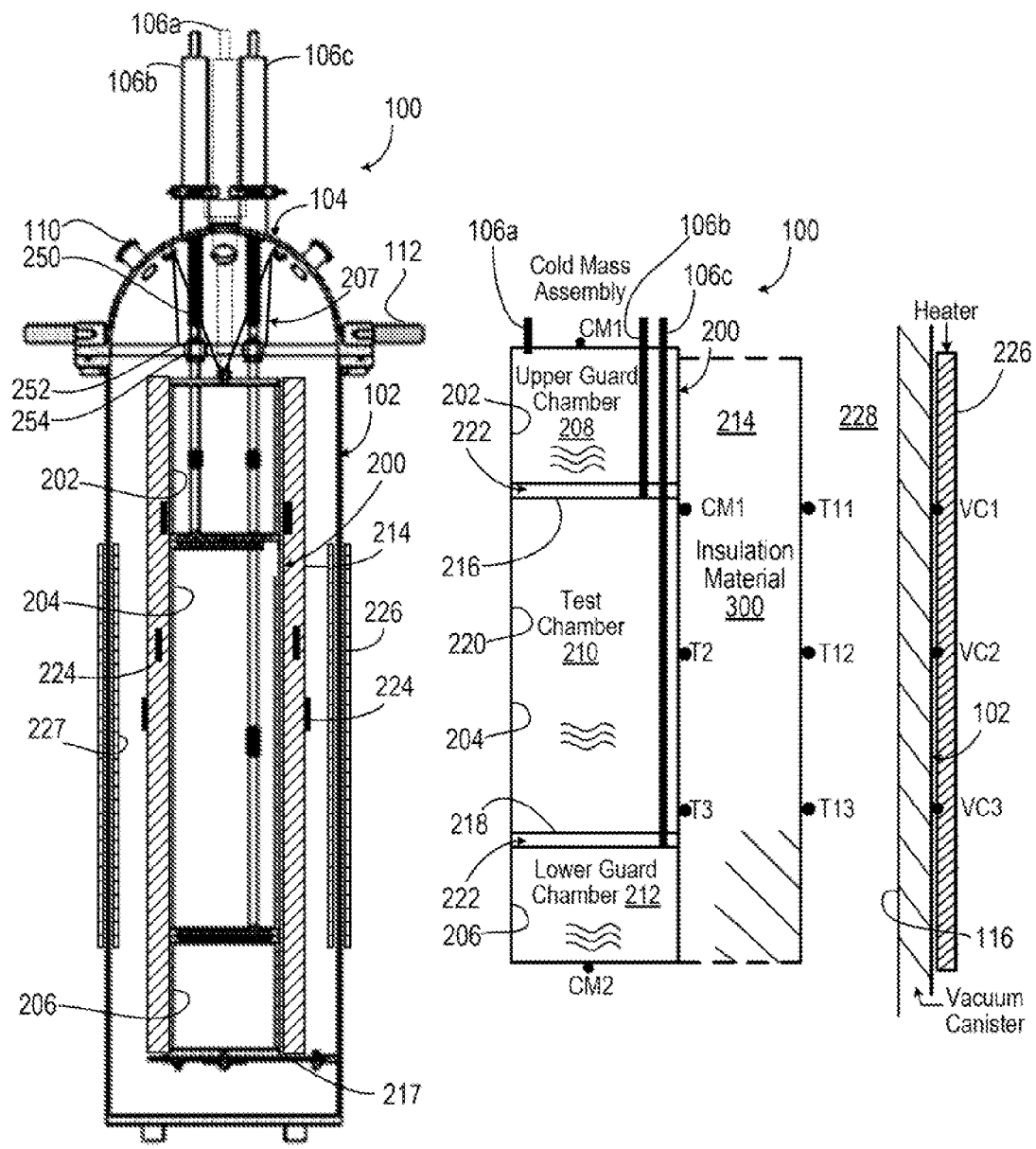
FIG. 2 illustrates a cutaway view of the cryogenic testing apparatus of FIG. 1.

In FIG. 2, the vacuum canister 102 encompasses a cylindrically shaped cold mass assembly 200 having a vertically assembled stack of three cylinders, specifically an upper vessel 202, an inner vessel 204, and a lower vessel 206. The cold mass assembly 200 is suspended by string suspension lines 207 made of polymer fibers such as KEVLAR (or stainless steel wire) from the lid 104 inside the vacuum canister 102 to form the Cryostat-100 apparatus 100.

The three feedthroughs 106a-106c communicate to fill and vent respectively at the same time through a given port, an upper guard chamber 208 of the upper vessel 202, a test chamber 210 of the inner vessel 204, and a lower guard chamber 212 of the lower vessel 206.

In FIG. 2, Each of the elongate feedthroughs 106a-106c comprises a respective bellows 250 of sufficiently thin-wall construction for low thermal conduction and mechanical compliance, each bellows 250 comprising an upper bellows connection 252 and a lower bellows connection 254. The upper and lower bellows connection 252, 254 is dimensioned to enable full cryogenic temperature and high vacuum pressure compatibility with minimal leakage and enable removal of the cold mass assembly from the top lid 104. The upper and lower bellows connection further comprises a precision spherical face seal metal-gasketed fittings.

The simultaneous filling and venting through a single port is achieved by inserting the funnel assembly 155 including a funnel (fill) tube 157 (FIG. 1) of a certain diameter and with a plurality of holes of certain sizes and positions along the tube. The clearance between the outer diameter of the fill tube and the inner diameter of the feedthrough tube provides the pathway for the vent gas. The holes in the fill tube provide an optimized balance between cold gas spray effect for more rapid cool down and liquid delivery for more rapid filling and refilling of the cold mass chambers.

Feedthrough 106a is depicted by phantom lines to indicate residence in a cutaway portion of the vacuum canister 102 that was otherwise omitted. Each chamber 208-212 receives a cryogenic liquid (cryogen), for example liquid nitrogen (LN2), helium (LHe), hydrogen (LH2), methane, or other known refrigerants. Any suitable liquid with a boiling point below ambient temperature may be used with appropriate facility adaptations.

For LH2 or LHe, the system would be essentially the same. The materials of construction can be the same and the fabrication techniques can be the same. At normal atmospheric pressure of 14.7 psia (760 torr), LH2 boils at 20 K and LHe at 4.2 K. The cold mass assembly could be made lighter weight, by an appropriate combination of materials and construction methods, just to save on the consumption of helium during cool down.

The apparatus incorporates a number of design features that minimize heat leak, except through specific portions of the inner vessel 204. For example, the upper and lower guard chambers 208, 212 ensure thermal stability and complete thermal isolation of the cryogenic environment of the test chamber 210. The cold mass assembly 200 receives a cylindrical test specimen 214 onto its external vertical surface. A sleeve support and guide 217 is attached to the lower guard chamber 212 to provide support to the test specimen 214 and keep the cylindrically shaped cold mass assembly 200 centered in the cylindrical portion 116 of the vacuum canister 102. The heat leak rate through top 216 and bottom 218 of the inner vessel 204 is reduced to a very small fraction of the heat leak through a cylindrical sidewall 220 of the inner vessel 204. Cold gas vapor pockets 222 in the top 216 and bottom 218 provide additional thermal separation to achieve complete thermal isolation during final steady-state operation of the assembly.

Temperature sensors (e.g., thermocouples) 224 are placed between layers of the testing material of the test specimen 214 (e.g., foam, bulk fill, multi-layer insulation (MLI), blanket, clam-shell forms) that is wrapped around the cold mass assembly 200 to obtain temperature-thickness profiles. An aluminum sleeve (not shown) is used to test bulk-fill materials. The black coated high emissivity sleeve provides a nominal annular space gap into which the material is poured. Several fiberglass rings at both top and bottom keep the material in place. Alternatively, the test specimen 214 can be molded, for example two half cylindrical sleeves (not shown) held to the cold mass assembly 200 by band clamps or tape. The effective thermal conductivity (k-value) of the testing material is determined by measuring the boil-off flow rate of the cryogenic fluid and temperature differential between a cold boundary temperature and a warm boundary temperature for a known thickness of the testing material. A heater 226 on the entire outer surface of the vacuum canister 102 provides bake-out of the test specimens and basic warm boundary control. An internal heater 227 is attached inside the vacuum canister 102 to provide fine temperature and heating control to establish the precise warm boundary temperature required for the test (293 K+/−0.3 K is typical). The internal heater system is composed of several thin-film type flexible heating elements attached to the outer surface of an aluminum sleeve that extends the length of the cold mass within. This sleeve is a high-emissivity black coated internal surface to direct the maximum heat energy toward the cold mass and therefore decrease the power levels and improve system control. The sleeve assembly is held in place inside the inner wall of the vacuum can by plastic composite (for example, G-10 fiberglass epoxy composite) stand-offs. Warm boundary temperatures from about 100 K to 400 K are possible, with 250 K to 350 K being most typical. A vacuum 228 is maintained inside of the vacuum canister 102.

In an exemplary embodiment, the cold mass assembly 200 undergoes acceptance testing by X-ray weld inspection, liquid nitrogen cold shock, helium mass spectrometer leak test, and vacuum retention testing. The cold mass assembly 200 has a surface finish of a black chrome test chamber portion 210 and electropolished upper and lower guard chamber portions 208, 212.

Figure 3:
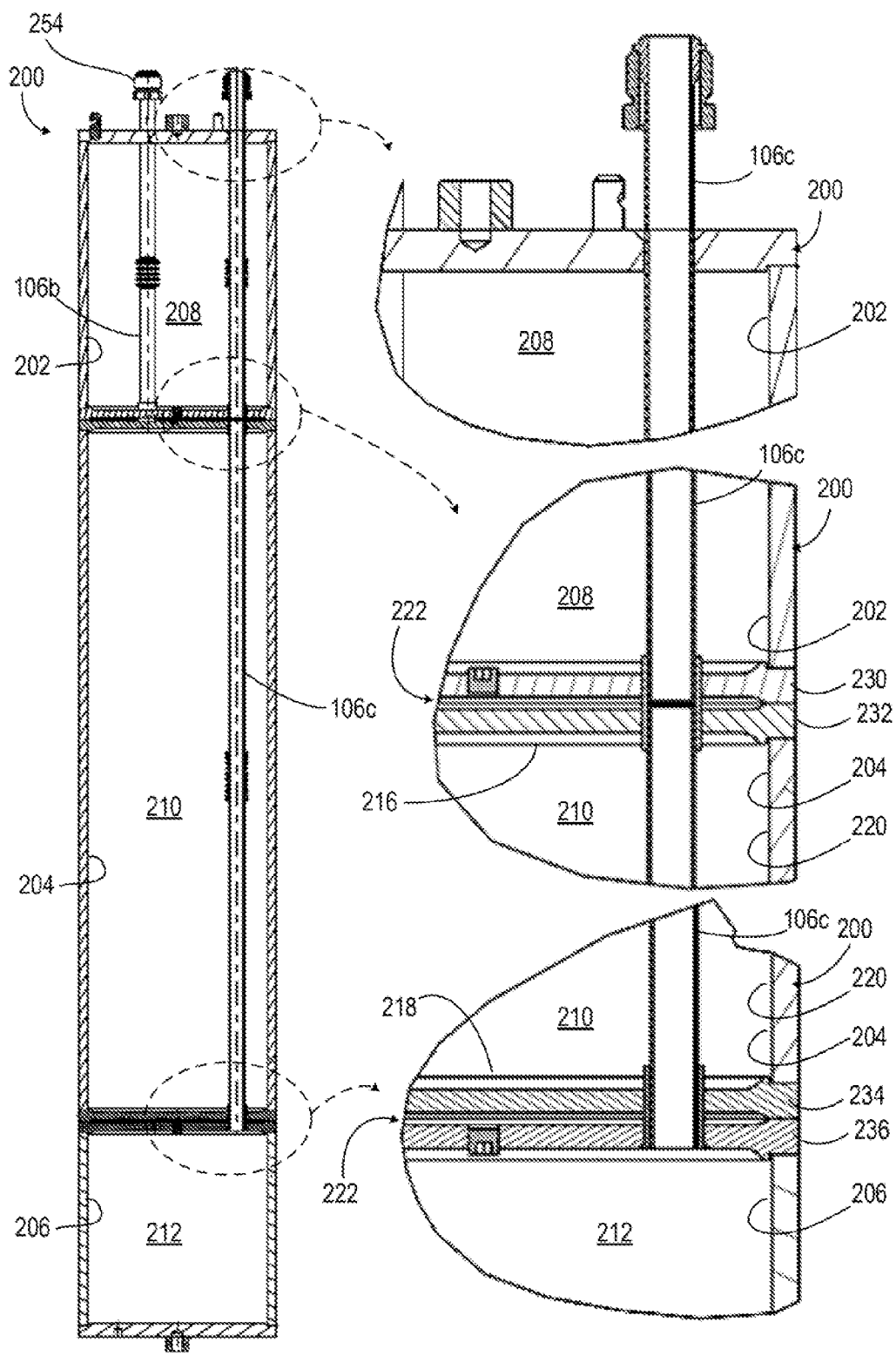
FIG. 3 illustrates a cutaway view of a cold mass assembly of the cryogenic testing apparatus of FIG. 2 with detail views.

In FIG. 3, the cold mass assembly 200 in an exemplary embodiment is assembled to create the upper, inner and lower vessels 202, 204, 206 that include cold gas vapor pockets 222 there between. In particular, the top 216 of the inner vessel 204 is formed from a top disk 230 welded around its circumference to a lower disk 232, each presenting a concave surface to the other to define the cold gas vapor pocket 222. Similar, the bottom 218 of the inner vessel 204 is formed from a top disk 234 welded around its circumference to a lower disk 236, each presenting a concave surface to the other to define the cold gas vapor pocket 222. The pockets are filled with carbon dioxide or other condensable gas such that a vacuum is created when the cold mass is filled with the cryogenic liquid (cryogen). This device then provides thermal isolation between either liquid volume in the guard chambers and the liquid volume of the test chamber. The thermal isolation is obtained by precluding direct solid conduction heat transfer from one liquid volume to another. Isolation is further enhanced by the insulation effectiveness of the pocket itself as the cryogenic conditions produce a high-vacuum condition within and a corresponding high level of thermal insulating performance. This isolation is critical for the very low heat measurement capability to be achieved as small variations in liquid temperatures between chambers can easily lead to dramatically negative consequences (e.g., axial heat conduction) on the fine heat rates that must be measured radially through the thickness of the insulation specimen and into the cold mass test chamber.

By contrast, prior approach required a carefully supervised, lengthy methodology with complex ancillary equipment and was prone to non-optimal results. In particular, vapor pockets in the cryogenic chambers were created to produce thermal isolation required for fine stability. However, the methodology entailed phasing of operations to accomplish the vapor pockets. Flow to the chambers was stopped at just the right times and in just the right order to produce small ullage spaces in the chambers.

By having bulk-head plates welded together with a cavity in between filled with $CO_2$, no servicing is required during their useful lifetime. Alternatively, an insulation material such as aerogel granules could be installed between two plates for any combination of decreased heat transfer, increased structural integrity, and increased acoustic absorption. Applications for such compact, lightweight and/or more aerodynamic design can be used for any precision measuring equipment or device requiring heat transfer isolation between two chambers of like fluids. Alternatively or in addition, such vapor pocket containing devices can be used in common bulkhead cryogenic tank constructions for future launch vehicles or space craft.

Figure 4:
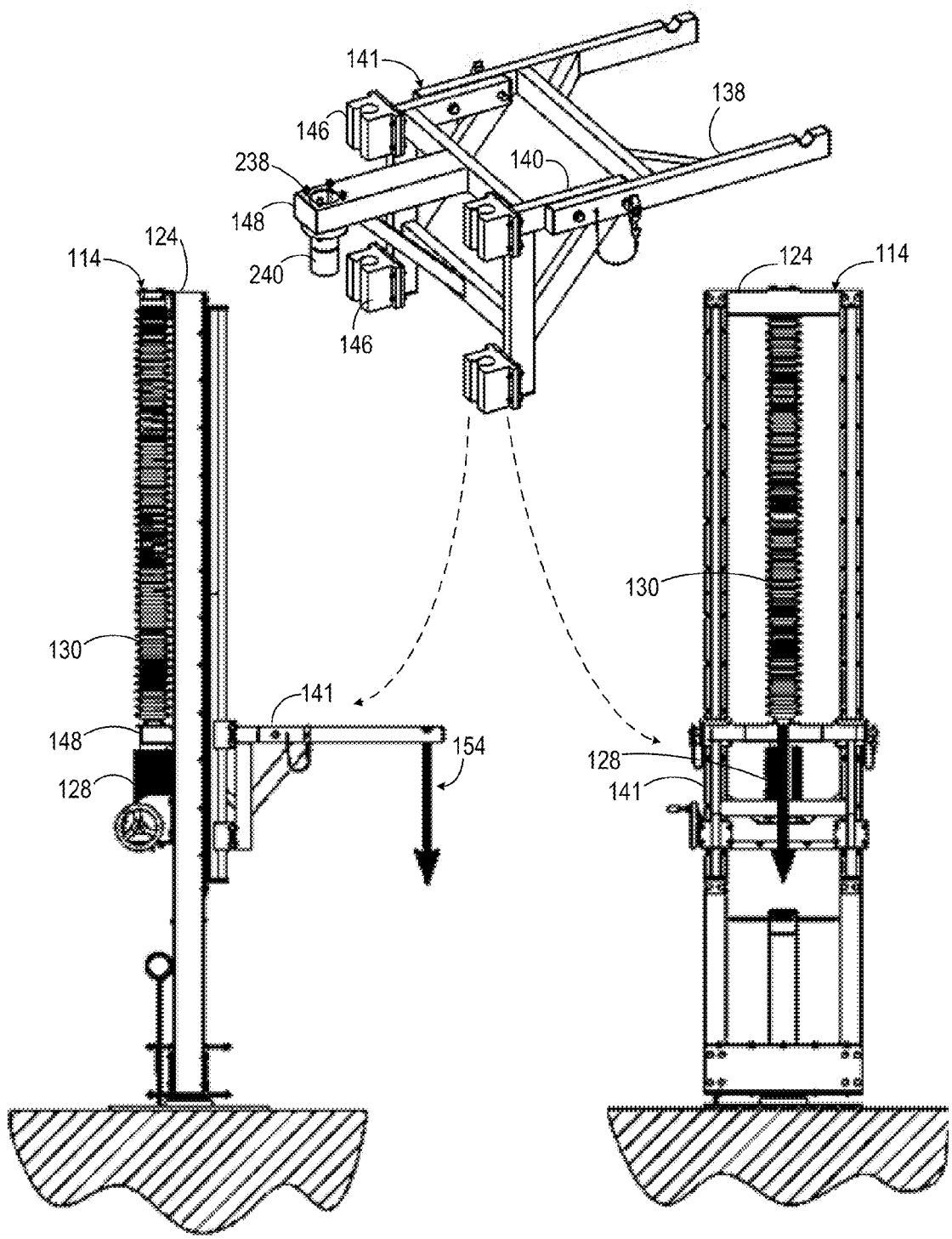
FIG. 4 illustrates a side and front view of the lifting mechanism of FIG. 1 with an isometric view of a carriage.

In FIG. 4, the lift mechanism 114 is depicted. The carriage 141 is removed from the frame 124 to show that the actuator arm 148 proximally presents a vertical hole 238 aligned with a downwardly projecting sleeve 240, the latter sized to be received within the bellows 128 and providing an elongate inner diameter for presenting inner diameter threads (not shown) to engage outer diameter threads of the machine screw jack 130.

Figure 5:
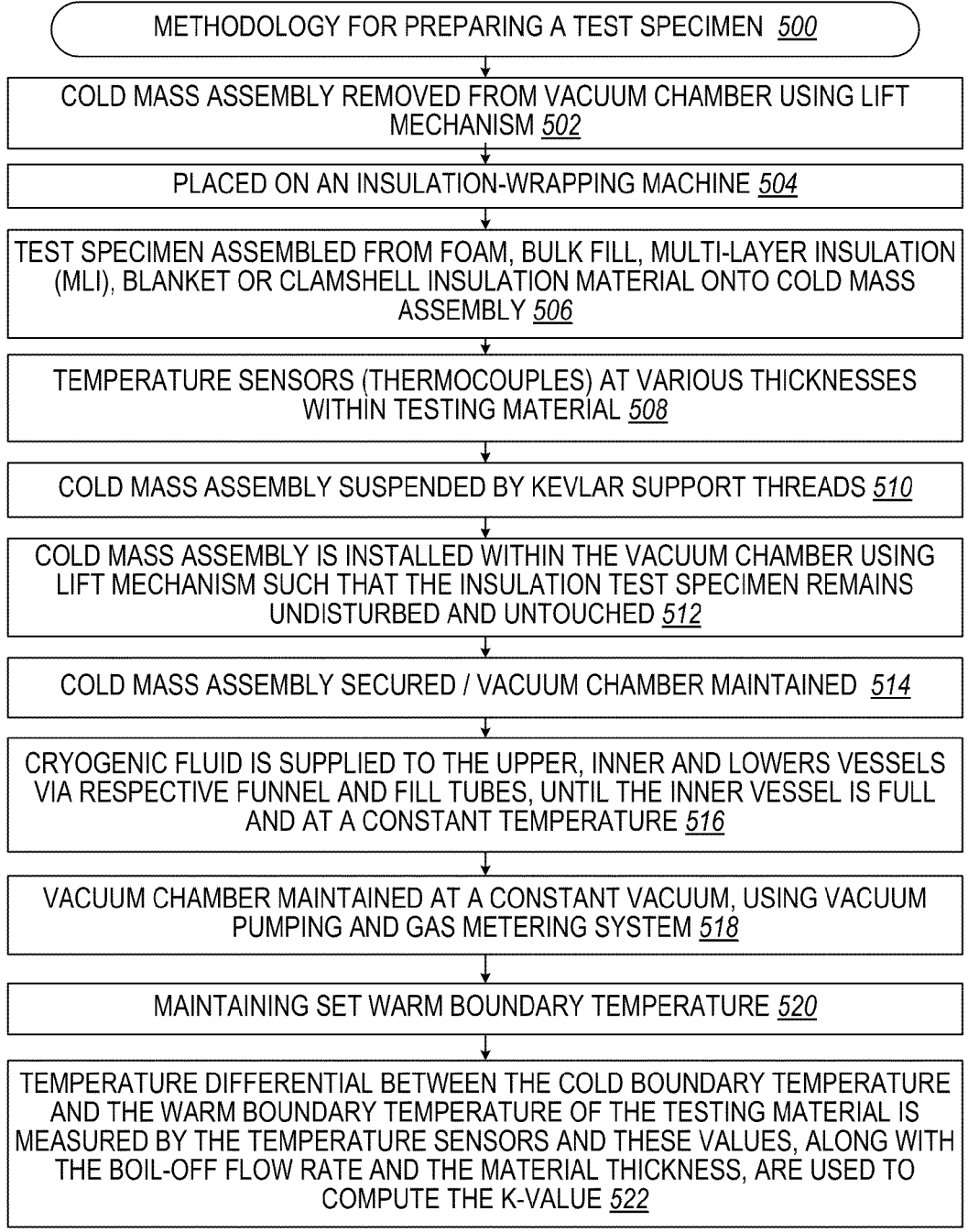
FIG. 5 illustrates a flow diagram of a methodology or sequence of operations for preparing a test specimen.

In FIG. 5, a methodology or sequence of operations 500 is depicted for preparing a test specimen. During an exemplary use, the cold mass assembly is easily and quickly removed from the vacuum chamber by using the lift mechanism (block 502) and positioned as needed for reconfiguration. The cold mass can be further removed from the lid and placed on a vertical or horizontal insulation-wrapping machine such as by using special handling tools (block 504). Alternatively or in addition, the test specimen can be assembled from foam, bulk fill, multi-layer insulation (MLI), blanket, clam-shell, or other form insulation material onto the cold mass assembly (block 506). A composite circular plate (G-10 material) is optionally attached to be bottom end of the cold mass. This plate serves as vertical resting point for the insulation material and also as a guide for the cold mass assembly while being lowered into the vacuum can. A black sleeve (aluminum) with stand-offs comprised of multiple layers of micro fiberglass rings (donuts) on each end are used to hold a bulk-fill material in place. For example, using an effective length of the cold mass of 575 mm, the mean surface area for heat transfer through a typical 25-mm thick insulation test article is 0.35 $m^2$.

Temperature sensors, such as thermocouples, are optionally placed at various thicknesses within the testing material (block 508). A first temperature sensor on the inner vessel is designated the cold boundary temperature sensor. The cold boundary temperature is preferably determined from the known saturation temperature and pressure of the cryogenic liquid or other test liquid. A second temperature sensor on the outer surface of the testing material is designated the warm boundary temperature sensor. The warm boundary temperature sensor may be placed at any known distance from the inner vessel but is normally placed on the outer surface of the insulation test specimen. Three or more temperature sensors may be placed along a vertical line to provide information for more improved heater control in establishing the warm boundary temperature. The warm boundary in other designs may be established by the environmental temperature of the vacuum can such as may be provided by ambient air, a fluid bath, or other conventional heat exchange methods. Sensors are typically placed between any or all layers of the insulation to obtain complete temperature profiles. Steady-state measurement of insulation performance is made when all temperatures and the boil-off flow are stable. The k-value of the insulation is directly determined from the measured boil-off rate, temperature difference (WBT–CBT), latent heat of vaporization, and geometry of the insulation. All measurements are preferably recorded on an automatically recording data acquisition system.

In an exemplary embodiment, test materials are installed around a cylindrical copper sleeve using a custom-built 1-meter wide wrapping machine. Testing of blanket, multi-layer insulation, and continuously rolled specimens is facilitated by the sleeve employed in the Cryostat-100. Insulation test articles 167-mm inside diameter by 1000-mm-in length up to 70-mm-in thickness can be fabricated and tested. After fabrication of the insulation system, the sleeve is simply slid onto the vertical cold mass of the Cryostat-100. The gap between the cold mass and the sleeve measures less than 1 mm. An interface material such as thermally conductive grease may also be applied within the gap to ensure good thermal contact between the cold mass and the test specimen.

After the testing material is secured to the cold mass assembly, the cold mass assembly is installed within the vacuum chamber using lift mechanism such that the insulation test specimen remains undisturbed (block 510). In an exemplary embodiment, the cold mass assembly is suspended by a plurality of support threads or wires, such as six KEVLAR threads with hooks and hardware for attachment and length adjustment prior to insertion into the vacuum chamber (block 512). KEVLAR threads have a low thermal conductivity, a high tensile strength and greatly resist elongation. Therefore, a relatively small diameter KEVLAR thread minimizes any additional heat transfer to the inner vessel. Hooks are designed to avoid wear damage to the threads.

Once the cold mass assembly is secure, the vacuum chamber is sealed (block 514), the cryogenic fluid is supplied to the upper, inner and lower vessels via respective funnel and fill tubes, until the inner vessel is full and at a constant temperature (block 516). The vacuum chamber is maintained at a constant vacuum, using an exemplary vacuum pumping and gas metering system (block 518), and a set sidewall temperature, using a preferred electrical heater system (block 520).

The temperature differential between the cold boundary temperature and the warm boundary temperature of the testing material is measured by the temperature sensors and these values, along with the boil-off flow rate and the material thickness, are used to compute the k-value (block 522). While calibration of the device is not required, verification of zero heat leak rates through the ends, or "end effects" can be accomplished by testing a material with a known k-value under the pressure and temperature conditions of interest.

Figure 6:
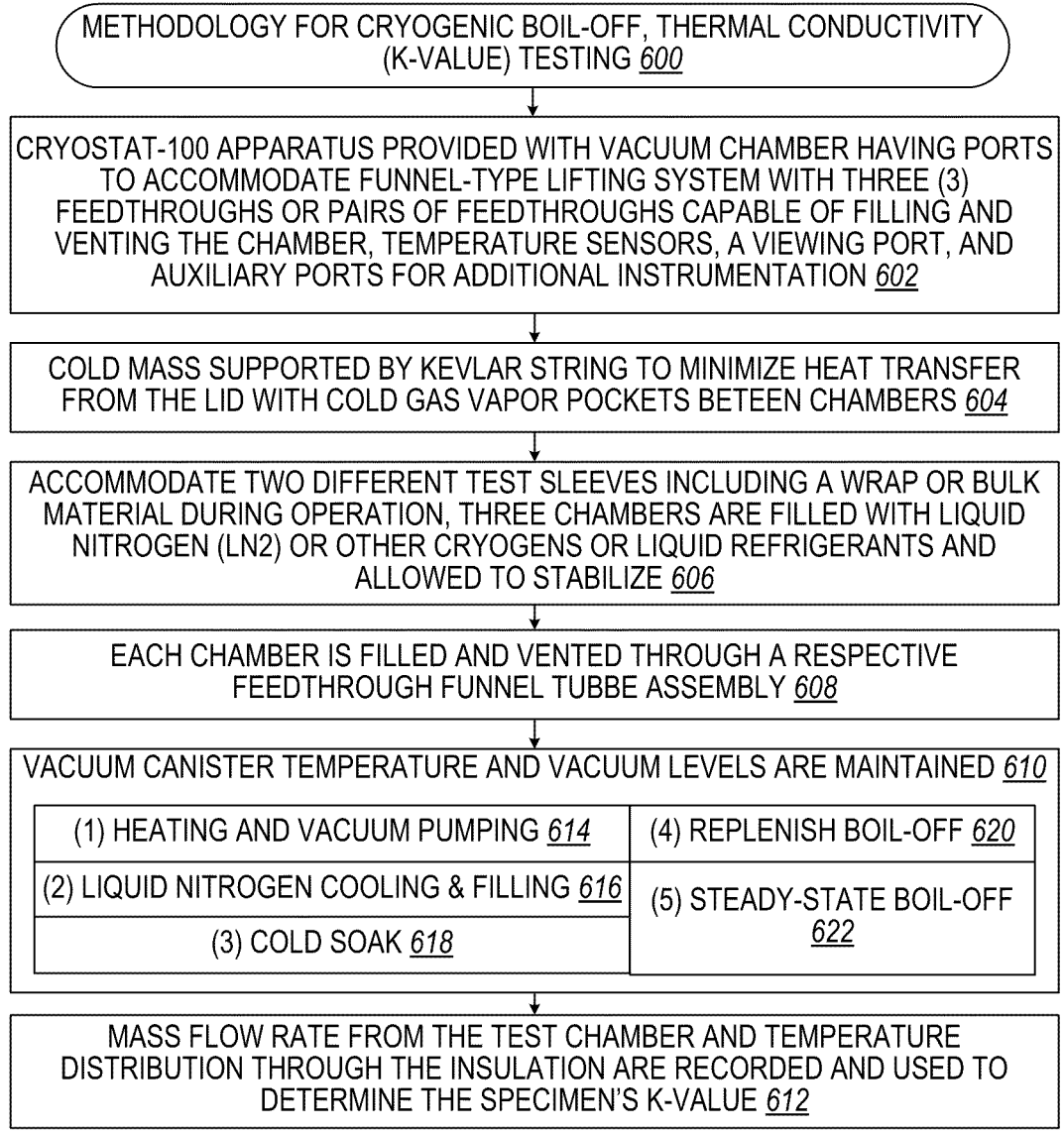
FIG. 6 illustrates a flow diagram for a methodology or sequence of operations for cryogenic boil-off, absolute thermal conductivity testing.
Figure 7:
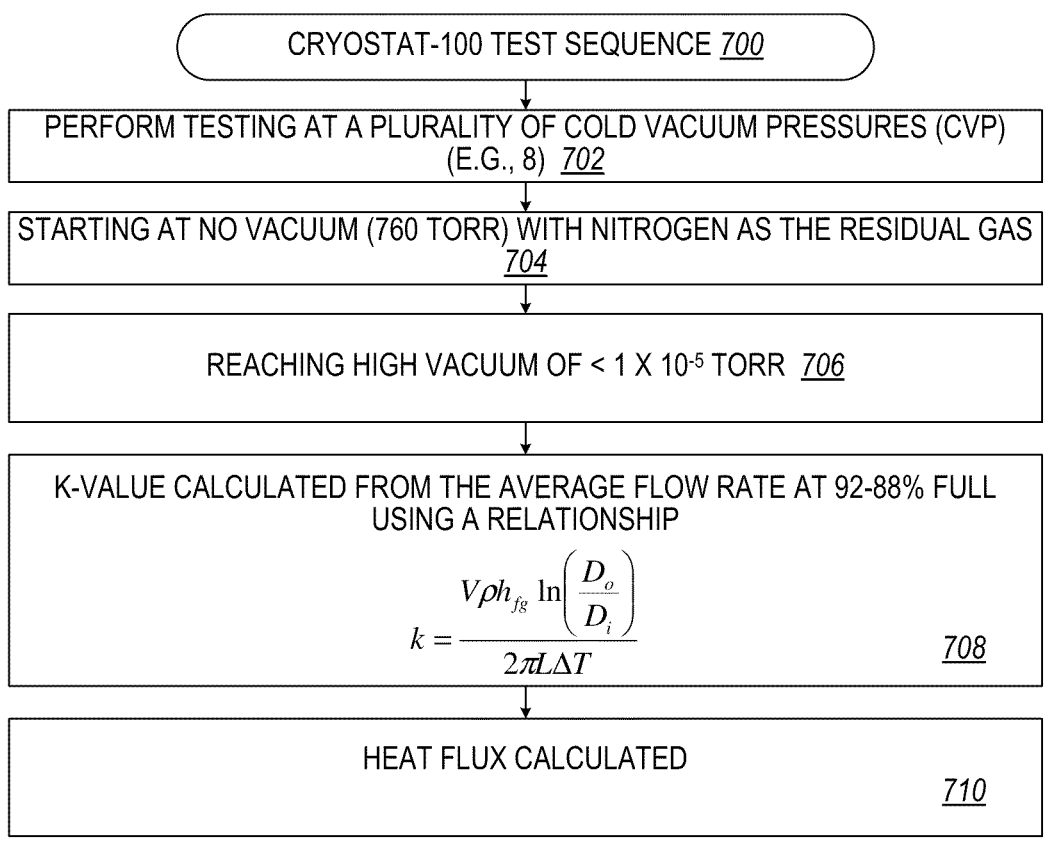
FIG. 7 illustrates a flow diagram for a cryogenic test procedure.

In FIG. 6, an exemplary methodology or sequence of operations 600 is provided for cryogenic boil-off, cylindrical absolute thermal performance testing. The Cryostat-100 apparatus is provided with a vacuum chamber having ports to accommodate funnel-type filling system with three (3) feedthroughs (pairs of feedthroughs), capable of the combination filling and venting of each of the three chambers. There are temperature sensors (e.g., 15 pairs of thermocouple lead wire conductors), a viewing port, and auxiliary ports for additional instrumentation (block 602). The cold mass is supported by strings or thin wires to minimize heat transfer from the lid and cold gas vapor pockets are provided between chambers to eliminate heat transfer from either end into the test chamber (block 604). The device may accommodate any number of different test sleeves and any type of material form including a wrap, continuously rolled, bulk, loose-fill, clamshell, panels, and other forms of material. Materials can be isotropic, multi-layered, combinations, or composites. During operation of the Cryostat-100 apparatus, three chambers are cooled and then filled with liquid nitrogen (LN2), liquid hydrogen (LH2), liquid helium (LHe), or other cryogens or liquid refrigerants and allowed to stabilize (block 606). In an exemplary embodiment, each chamber is filled and vented through a respective feedthrough funnel tube assembly (block 608). Vacuum canister temperature and vacuum levels are maintained (block 610). Mass flow rate from the test chamber and temperature distribution through the insulation are recorded and used to determine the specimen's k-value (block 612). Generally, the k-value and heat flux are calculated and these are directly proportional to the boil-off flow rate. Boil-off flow rates for the upper guard chamber and the lower guard chamber are also recorded to provide additional information in controlling the test and verification of unidirectional heat transfer through the thickness of the test specimen as well as overall thermal stability of the system.

During testing of block 610, five operational sequences may be performed including:

(1) Heating and vacuum pumping (block 614);
(2) Liquid nitrogen cooling and filling (block 616);
(3) Cold soak (block 618);
(4) Replenish boil-off (block 620); and
(5) Steady-state boil-off (block 622).

Initial cool down of the cold mass assembly is achieved in approximately two hours. Complete cool down and thermal stabilization through the thickness of the insulation test specimen may require from 2 to 200 hours or perhaps more depending on the level of thermal performance of the test specimen. It should be appreciated that quick duration tests can also be performed to achieve good data, although the results may not be necessarily certified against prior tests or standard reference data. During cool down and stabilization, all three chambers are replenished as necessary to maintain them approximately full. Liquid levels may range from approximately half full to full without compromise to the success of the cool down and stabilization phase. Boil-off flow rates for all three chambers are continuously monitored during this time by maintaining connection via flexible plastic tubing to the three mass flow meters. The level of back-pressure on the chambers, while not critical to the operation, must be maintained consistently and similarly for all three chambers. The similar back-pressures are achieved simply by keeping all three connecting tubes (inner diameter and length), connecting hardware, and flow meter types the same. These three flows may be further connected to a single reservoir to singularly and simultaneously regulate the back-pressure on all the liquid chambers so that periodic atmospheric pressure variations are either eliminated or minimized to an acceptable level.

In an exemplary embodiment, heavy stainless steel construction with integral vapor pockets provides stratified (not mixed) liquid condition in all three chambers. Thereby, the prior art problems associated with re-condensation of test chamber boil-off vent gas is avoided. Ultra-critical chamber pressure regulation and complex control systems, required in the prior art of boil-off testing, is completely eliminated by the Cryostat-100 design. At very low heat flux levels, the daily cyclic variations in barometric pressure can cause a similar cyclic pattern in the boil-off test result. But this effect is eliminated or minimized by discharging all three vent flows into a common reservoir surge vessel that is maintained at a slightly higher pressure above the prevailing room pressure (a delta pressure of about 4 millibar is sufficient for most locations). Back pressure regulation is generally required for very low heat transfer rate testing and is generally unnecessary for medium to high heat transfer rate tests.

While test operations utilizing the Cryostat-100 may be lengthy in duration, the actual operation of the Cryostat-100 apparatus 100 requires little operator intervention. Consequently, production of new engineering data and scientific information is much more cost effective. The design of the Cryostat-100 apparatus 100 is fully modular, portable, repeatable, and adaptable to different fluids or environmental test conditions. The Cryostat-100 apparatus 100 is particularly well suited for testing a wide variety of materials including, but not limited to, bulk fill, powders, multilayer, foams, clamshells, layered composites, etc. The device is easily adapted to utilizing different boundary temperatures up to 400 K and any cold boundary temperature above 77 K when using liquid nitrogen as the test liquid. Minor adaptations in material selection and facility details can allow cold boundary temperatures of 20 K (liquid hydrogen) or 4 K (liquid helium). The data obtained from utilization of the Cryostat-100 apparatus 100 is to a level of accuracy that it creates standard reference material for the calibration of conventional insulation test equipment. Other cold boundary temperatures could be designed for 216 K (carbon dioxide), 246 K (Freon R134a), 351 K (ethyl alcohol), and other known refrigerants with suitable boiling points and latent heats of vaporization.

In one exemplary embodiment, a Cryostat-100 test procedure can provide for a minimum of eight (8) Cold Vacuum Pressure (CVP) values (block 702), starting at no vacuum (760 torr) with nitrogen as the residual gas (block 704), working down to high vacuum (<1×10-5) (block 706). The k-value calculated from the average flow rate at 100-99% or 92-88% full, depending on the heat transfer range, using a relationship $$k = \frac{V \rho h_{fg} \ln\left(\frac{D_o}{D_i}\right)}{2\pi L \Delta T} \text{(block 708),}$$

where
k is effective thermal conductivity (k-value),
L is effective heat transfer length of the cold mass inner vessel,
$h_{fg}$ is heat of vaporization of the refrigerant,
$D_o$ is outer diameter of the insulation (warm boundary),
$D_i$ is inner diameter of the insulation (cold boundary), ρ(rho) is a density of the boil-off gas under standard conditions, V is a volumetric flow rate of boil-off gas, ΔT is full temperature difference between warm boundary surface and cold boundary surface, which in the exemplary implementation is based upon Cold-Boundary Temperature (CBT), 78 K; Warm-Boundary Temperature (WBT), 293 K; to result in ΔT Temperature difference, 216 K, and Full-range Cold Vacuum Pressure (CVP) is between High vacuum (HV), below 1×10-5 torr and Soft vacuum (SV), ~1 torr with No Vacuum (NV), 760 torr. Similarly, the thermal flux can be calculated (block 710), for which an exemplary calculation follows.

In FIG. 8, a methodology 800 utilizing a spreadsheet for calculating mean heat transfer rate for concentric cylindrical geometry is depicted in spreadsheet form for an exemplary set of input data. The methodology 800 utilizes the following relationships:

$Am$=Mean Heat Transfer Area (m2)

$Am=(Ao-Ai)/LN(Ao/Ai)$ $Q$=Heat Transfer Rate (W)

$Q=k*Am*(WBT-CBT)/DX$ $q=Q/Am$=Heat Flux Rate (W/m2)

$q=k*(WBT-CBT)/DX$

Calculate Area:

$Ao$=Outside Insulation Surface Area $Ao=\pi*Do*L$ $Ai$=Sleeve Outside Surface Area $Ai=\pi*Di*L$ $Am=(Ao-Ai)/LN(Ao/Ai)$ $(Ao-Ai)=\pi*L*(Do-Di)=2*\pi*L*(DX)$ $Am=2*\pi*L*(DX)/LN(Do/Di)$ Calculate Heat Q $Q=h*m$ $Q=\{k*/2*\pi*L*(DX)/LN(Do/Di)]*[(WBT-CBT)]/DX\}$ $Q=2*\pi*k*L*(WBT-CBT)/LN(Do/Di)$ Calculate Heat Flux q $q=Q/Am=k*(WBT-CBT)/DX$ Calculate apparent thermal conductivity k $k=h*m*LN(Do/Di)/2*\pi*L*(WBT-CBT)$ The following TABLE 2 is an exemplary reference for gaseous nitrogen (GN2) that can be utilized in these calculations:

TABLE 2

Density of nitrogen gas at STP
0 deg C. and 760 torr
(reference for massflow meters)
101.3 kPa & 273 K gives 0.0012502 g/cm^3
14.696 psia & 492 R gives 0.078009 lbm/ft^3
Gaseous Nitrogen (GN2)

| Saturation pressure psig | saturation temperature K | Heat of Vaporization (Hfg) J/g |
|---|---|---|
| 0.0 | 77.4 | 199.3 |
| 0.1 | fix | 198.6 |
| 0.2 |  | 198.0 |
| 0.3 |  | 197.3 |
| 0.4 |  | 196.6 |
| 0.5 |  | 196.0 |
| 0.6 |  | 195.3 |
| 0.7 |  | 194.6 |
| 0.8 |  | 193.9 |
| 0.9 |  | 193.3 |
| 1.0 |  | 192.6 |

Cryostat-100 was proven in a Cryogenics Test Laboratory to provide thermal characterization of the materials in terms of absolute thermal conductivity (k-value). Test articles were cylindrical (foam, bulk fill, multilayer insulation (MLI), blanket), each of approximate 25-mm thickness.

The following 29 pairs of tables provide illustrative empirical data for these various types of insulation specimens.

TABLE A102-a

| A102 Glass Bubbles 65 25-mm Bubbles | CVP (microns) | k-value (mW/m-K) | Qtot (W) | Q/Am Heat Flux (W/m2) | Flow Rate (sccm) | WBT (K) |
|---|---|---|---|---|---|---|
|  | 0.0022 | 0.697 | 2.054 | 5.893 | 496 | 292.8 |
|  | 0.003 | 0.694 | 2.043 | 5.862 | 493.723 | 292.632 |
|  | 0.1 | 0.695 | 2.049 | 5.879483501 | 495.156 | 293.013 |
|  | 1 | 0.711 | 2.096 | 6.014347202 | 506.403 | 292.904 |
|  | 2 | 0.739 | 2.188 | 6.278335725 | 528.785 | 293.713 |
|  | 5 | 0.763 | 2.246 | 6.444763271 | 542.729 | 292.588 |
|  | 10 | 0.83 | 2.448 | 7.024390244 | 591.635 | 292.949 |
|  | 10 | 0.82 | 2.419 | 6.941176471 | 584.524 | 293.095 |
|  | 25 | 0.968 | 2.861 | 8.209469154 | 691.42 | 293.327 |
|  | 50 | 1.224 | 3.62 | 10.38737446 | 874.875 | 293.585 |
|  | 102 | 1.704 | 5.048 | 14.48493544 | 1219.792 | 293.838 |
|  | 200 | 2.675 | 7.903 | 22.67718795 | 1909.807 | 293.316 |
|  | 349 | 3.773 | 11.158 | 32.01721664 | 2696.372 | 293.536 |
|  | 350 | 3.857 | 11.409 | 32.7374462 | 2757.017 | 293.588 |
|  | 993 | 7.737 | 22.872 | 65.62984218 | 5527.103 | 293.446 |
|  | 998 | 7.779 | 22.953 | 65.86226686 | 5546.57 | 293.047 |
|  | 3002 | 13.764 | 40.535 | 116.312769 | 9795.309 | 292.649 |
|  | 9960 | 19.894 | 59.051 | 169.4433286 | 14269.927 | 294.339 |
|  | 9988 | 19.84 | 58.602 | 168.1549498 | 14161.461 | 293.278 |

-continued

| | | | | | |
|---|---|---|---|---|---|
| 30027 | 22.803 | 67.427 | 193.4777618 | 16294.025 | 293.512 |
| 99882 | 25.089 | 73.913 | 212.0889527 | 17861.372 | 292.714 |
| 99943 | 25.171 | 74.358 | 213.3658537 | 17968.836 | 293.301 |
| 760000 | 25.608 | 75.763 | 217.3974175 | 18308.423 | 293.631 |
| 760000 | 26.053 | 77.246 | 221.6527977 | 18666.624 | 294.092 |

TABLE A102-b

| Tfinal mm | OD mm | ID mm | Height mm | Mass g | Density g/cc |
|---|---|---|---|---|---|
| 25.40 | 217.90 | 167.10 | 720.70 | 885.6 | 0.080 |

TABLE A103-a

| A103 Perlite Powder 132 25-mm Perlite | CVP (m) | CVP (m) | k (mW/m-K) | Qtot (W) | Q/Am (W/m2) | Flow (sccm) | WBT (K) |
|---|---|---|---|---|---|---|---|
| | 0.001 | 0.001 | 0.936 | 2.756 | 7.908177905 | 665.882 | 292.573 |
| | 0.1 | 0.1034 | 0.953 | 2.808 | 8.057388809 | 678.642 | 292.731 |
| | 0.5 | 0.4936 | 0.955 | 2.81 | 8.06312769 | 679.134 | 292.519 |
| | 1 | 0.9982 | 0.999 | 2.945 | 8.450502152 | 711.566 | 292.881 |
| | 5 | 5.0004 | 1.153 | 3.401 | 9.758967001 | 821.789 | 292.916 |
| | 10 | 10.0148 | 1.308 | 3.867 | 11.09612626 | 934.549 | 293.483 |
| | 25 | 24.9977 | 1.883 | 5.555 | 15.93974175 | 1342.341 | 293.038 |
| | 100 | 100.1024 | 3.814 | 11.261 | 32.31276901 | 2721.186 | 293.185 |
| | 1,000 | 1027.1 | 13.994 | 41.22 | 118.2783357 | 9961.001 | 292.679 |
| | 10,000 | 10042.1181 | 27.879 | 81.789 | 234.6886657 | 19764.548 | 291.821 |
| | 10,000 | 10009.7577 | 27.815 | 81.903 | 235.0157819 | 19792.102 | 292.607 |
| | 100,000 | 92341.1371 | 33.695 | 99.405 | 285.2367288 | 24021.457 | 293.015 |
| | 100,000 | 100038.0546 | 33.522 | 98.923 | 283.8536585 | 23905.112 | 293.077 |
| | 100,000 | 100025.5157 | 33.679 | 99.227 | 284.7259684 | 23978.425 | 292.734 |
| | 760,000 | 760000 | 34.737 | 102.482 | 294.0659971 | 24765.199 | 293.025 |
| | 760,000 | 760000 | 34.954 | 103.265 | 296.312769 | 24954.354 | 293.321 |

TABLE A103-b

| Tfinal mm | OD mm | ID mm | Height mm | Mass g | Density g/cc |
|---|---|---|---|---|---|
| 25.40 | 217.90 | 167.10 | 733.43 | 1875 | 0.166 |

TABLE A104-a

| A104 SOFI BX-265, NV to HV 1" BX-265, no rind | CVP (m) | CVP (m) | k (mW/m-K) | Qtot (W) | Q/Am (W/m2) | Flow (sccm) | WBT (K) |
|---|---|---|---|---|---|---|---|
| | 760,000 | 760000 | 21.17 | 59.69 | 171.276901 | 14424.321 | 292.794 |
| | 760,000 | 760000 | 21.142 | 59.61 | 171.0473458 | 14404.835 | 292.785 |
| NV to HV | 500,000 | 500000 | 20.383 | 57.661 | 165.4548063 | 13933.881 | 293.5 |
| | 500,000 | 500000 | 20.441 | 57.755 | 165.7245337 | 13956.589 | 293.239 |
| | 200,000 | 200000 | 20.188 | 57.098 | 163.8393113 | 13797.809 | 293.455 |
| | 200,000 | 200000 | 20.203 | 57.074 | 163.7704448 | 13792.199 | 293.211 |
| | 100,000 | 99991.5313 | 19.974 | 56.364 | 161.733142 | 13620.557 | 292.969 |
| | 100,000 | 99980.53 | 19.883 | 56.046 | 160.82066 | 13543.611 | 292.737 |
| | 10,000 | 10019.6892 | 19.848 | 56.004 | 160.7001435 | 13533.523 | 292.955 |
| | 10,000 | 9996.6013 | 19.729 | 55.642 | 159.661406 | 13446.147 | 292.851 |
| | 1,000 | 999.9946 | 19.692 | 55.628 | 159.6212339 | 13442.783 | 293.197 |
| | 1,000 | 1001.6359 | 19.535 | 55.14 | 158.2209469 | 13324.739 | 293.024 |
| | 100 | 100.0178 | 18.572 | 52.405 | 150.3730273 | 12663.848 | 292.96 |
| | 100 | 100.0433 | 18.313 | 51.692 | 148.3271162 | 12491.626 | 293.036 |
| | 100 | 100.0538 | 18.414 | 51.974 | 149.1362984 | 12559.637 | 293.016 |
| | 10 | 10.003 | 14.46 | 40.805 | 117.0875179 | 9860.588 | 292.974 |
| | 10 | 9.9839 | 14.524 | 40.977 | 117.5810617 | 9902.238 | 292.924 |
| | 1 | 1.002 | 8.738 | 24.658 | 70.75466284 | 5958.649 | 292.972 |

-continued

| | | | | | | | |
|---|---|---|---|---|---|---|---|
| | 1 | 0.9993 | 9 | 24.513 | 70.33859397 | 5923.609 | 293.072 |
| | 0.1 | 0.4293 | 8.235 | 23.058 | 66.16355811 | 5572.039 | 293.022 |

TABLE A104-b

| Tfinal mm | OD mm | ID mm | Height mm | Mass* g | Density g/cc |
|---|---|---|---|---|---|
| 26.70 | 220.60 | 167.10 | 1076.30 | 729.000 | 0.04157 |

*Mass after testing

TABLE A105-a

| A105 SOFI NCFI 24-124 1" NCFI 24-124, no rind | CVP (m) | CVP (m) | k (mW/m-K) | Qtot (W) | Q/Am (W/m2) | Flow (sccm) | WBT (K) |
|---|---|---|---|---|---|---|---|
| | 760,000 | 760000 | 21.162 | 61.822 | 177.3945481 | 14939.483 | 292.697 |
| | 760,000 | 760000 | 21.139 | 61.784 | 177.2855093 | 14930.408 | 292.797 |
| NV to HV | 500,000 | 497125.474 | 20.914 | 61.175 | 175.5380201 | 14783.149 | 292.967 |
| | 200,000 | 200694.9709 | 20.855 | 61.074 | 175.2482066 | 14758.767 | 293.219 |
| | 100,000 | 100066.0614 | 20.912 | 61.203 | 175.6183644 | 14789.795 | 293.081 |
| | 10,000 | 10012.5575 | 20.926 | 61.227 | 175.687231 | 14795.761 | 293.03 |
| | 1,000 | 1008.8108 | 20.161 | 58.932 | 169.1018651 | 14241.116 | 292.814 |
| | 1,000 | 1008.2997 | 20.345 | 59.511 | 170.7632712 | 14381.02 | 292.97 |
| | 100 | 100.0439 | 18.665 | 54.613 | 156.7087518 | 13197.464 | 293.037 |
| | 10 | 9.9961 | 13.396 | 39.189 | 112.4505022 | 9470.177 | 292.988 |
| | 10 | 10.0507 | 13.658 | 39.972 | 114.697274 | 9659.286 | 293.08 |
| | 1 | 1.661 | 9.207 | 26.937 | 77.29411765 | 6509.312 | 293.012 |
| | 1 | 1.3321 | 9.242 | 26.98 | 77.41750359 | 6519.773 | 292.547 |
| | 1 | 1.1988 | 9.195 | 26.878 | 77.12482066 | 6495.171 | 292.822 |
| | 1 | 1.0231 | 8.978 | 26.249 | 75.31994261 | 6343.164 | 292.854 |
| | 1 | 1.0487 | 9 | 26.306 | 75.48350072 | 6356.895 | 292.8 |
| | | 0.1578 | 7.466 | 17.741 | 50.90674319 | 4287.203 | 252.626 |

TABLE A105-b

| Tfinal mm | OD mm | ID mm | Height mm | Mass g | Density g/cc |
|---|---|---|---|---|---|
| 25.60 | 218.40 | 167.10 | 1037.20 | 607.000 | 0.03767 |

TABLE A106-a

| A106 SOFI NCFI 27-68 no rind | CVP (m) | CVP (m) | k (mW/m-K) | Qtot (W) | Q/Am (W/m2) | Flow (sccm) | WBT (K) |
|---|---|---|---|---|---|---|---|
| | 760,000 | 767300 | 20.746 | 64.738 | 165.3588761 | 15644.256 | 293.867 |
| | 760,000 | 765000 | 20.86 | 64.901 | 165.7752235 | 15683.442 | 293.228 |
| NV to HV | 760,000 | 763500 | 20.743 | 64.55 | 164.8786718 | 15598.71 | 293.272 |
| | 760,000 | 763500 | 20.8 | 64.838 | 165.614304 | 15668.366 | 293.648 |
| | 500,000 | 500000 | 20.711 | 64.403 | 164.5031928 | 15563.246 | 293.116 |
| | 500,000 | 500000 | 20.793 | 64.937 | 165.8671775 | 15692.262 | 294.047 |
| | 200,000 | 200000 | 19.818 | 61.642 | 157.4508301 | 14895.973 | 293.174 |
| | 100,000 | 100000 | 19.796 | 61.575 | 157.2796935 | 14879.914 | 293.179 |
| | 10,000 | 10000 | 19.554 | 60.834 | 155.3869732 | 14700.735 | 293.221 |
| | 1,000 | 990.3554 | 19.038 | 59.33 | 151.5453384 | 14337.354 | 293.584 |
| | 1,000 | 990.2368 | 18.953 | 59.061 | 150.8582375 | 14272.236 | 293.566 |
| | 100 | 100.0584 | 17.772 | 55.178 | 140.9399745 | 13334.052 | 292.787 |
| | 100 | 99.9785 | 17.725 | 55.09 | 140.715198 | 13312.558 | 293.01 |
| | 10 | 10.0295 | 13.21 | 41.059 | 104.8761175 | 9922.103 | 293.009 |
| | 10 | 9.9756 | 13.299 | 41.345 | 105.6066411 | 9991.057 | 293.064 |
| | 1 | 1.0017 | 8.051 | 25.018 | 63.90293742 | 6045.636 | 292.959 |
| | 0.1 | 0.9893 | 8.092 | 25.153 | 64.24776501 | 6078.403 | 293.022 |
| | 0.5 | 0.4888 | 7.334 | 22.791 | 58.21455939 | 5507.626 | 292.993 |
| | 0.5 | 0.4226 | 7.578 | 23.555 | 60.1660281 | 5692.256 | 293.031 |

-continued

TABLE A106-b

| Tfinal mm | OD mm | ID mm | Height mm | Mass g | Density g/cc |
|---|---|---|---|---|---|
| 24.4 | 216.00 | 167.10 | 1054.10 | 575.000 | 0.03707 |

TABLE A107-a

| A107 SOFI NCFI 24-124, with rind | CVP (m) | CVP (m) | k (mW/m-K) | Qtot (W) | Q/Am (W/m2) | Flow (sccm) | WBT (K) |
|---|---|---|---|---|---|---|---|
| NV to HV | 760,000 | 765000 | 24.145 | 73.789 | 187.662767 | 17831.353 | 293.107 |
| | 760,000 | 763500 | 24.052 | 73.436 | 186.7650051 | 17745.994 | 292.908 |
| | 760,000 | 764300 | 23.467 | 71.723 | 182.4084435 | 17332.099 | 293.128 |
| | 760,000 | 763500 | 23.678 | 72.366 | 184.0437436 | 17487.591 | 293.118 |
| | 760,000 | 762800 | 23.636 | 72.134 | 183.4537131 | 17431.504 | 292.817 |
| | 500,000 | 500000 | 23.119 | 70.538 | 179.3947101 | 17045.685 | 292.761 |
| | 500,000 | 500000 | 23.237 | 70.978 | 180.5137335 | 17152.151 | 292.998 |
| | 200,000 | 200000 | 22.857 | 69.775 | 177.4542218 | 16861.244 | 292.869 |
| | 100,000 | 101605.3336 | 22.576 | 68.926 | 175.2950153 | 16656.172 | 292.896 |
| | 100,000 | 100321.7679 | 22.599 | 68.973 | 175.4145473 | 16667.575 | 292.823 |
| | 10,000 | 10013.9647 | 22.506 | 68.64 | 174.5676501 | 16587.167 | 292.669 |
| | 10,000 | 10011.7247 | 22.464 | 68.456 | 174.0996948 | 16542.578 | 292.491 |
| | 1,000 | 1077.8122 | 21.948 | 67.009 | 170.4196338 | 16192.958 | 292.899 |
| | 1,000 | 1065.7659 | 22.189 | 67.733 | 172.2609359 | 16367.961 | 292.864 |
| | 100 | 99.9887 | 20.457 | 62.461 | 158.853001 | 15093.928 | 292.913 |
| | 100 | 99.9672 | 20.507 | 62.609 | 159.2293998 | 15129.577 | 292.89 |
| | 10 | 9.9855 | 14.261 | 43.546 | 110.7477111 | 10522.908 | 292.928 |
| | 10 | 10.0353 | 14.15 | 43.207 | 109.8855544 | 10441.036 | 292.923 |
| | 1 | 1.0102 | 8.712 | 26.597 | 67.64242116 | 6427.157 | 292.881 |
| | 1 | 1.0075 | 8.628 | 26.363 | 67.04730417 | 6370.681 | 293.071 |
| | 0.5 | 0.6046 | 8.453 | 25.797 | 65.60783316 | 6234.07 | 292.798 |
| | 0.5 | 0.554 | 8.502 | 25.957 | 66.01475076 | 6272.697 | 292.91 |

TABLE A107-b

| Tfinal mm | OD mm | ID mm | Height mm | Mass g | Density g/cc |
|---|---|---|---|---|---|
| 23.9 | 215.00 | 167.10 | 1074.70 | 589.000 | 0.03812 |

TABLE A108-a

| A108 Wh Beads 25-mm thick bulk fill | CVP (m) | Flow correct (sccm) | Qtot (W) | k (mW/m-K) | CVP (m) | WBT (K) | Q/Am (W/m2) |
|---|---|---|---|---|---|---|---|
| HV to NV | 0.001 | 1231.004 | 5.094 | 1.726 | 0.003 | 293.136 | 12.83770161 |
| | 0.001 | 1203.718 | 4.981 | 1.689 | 0.003 | 292.975 | 12.55292339 |
| | 0.001 | 1222.401 | 5.058 | 1.714 | 0.003 | 293.08 | 12.74697581 |
| | 0.1 | 1232.438 | 5.1 | 1.727 | 0.1268 | 293.228 | 12.85282258 |
| | 1 | 1303.095 | 5.392 | 1.828 | 0.9945 | 292.981 | 13.58870968 |
| | 10 | 1746.104 | 7.226 | 2.45 | 10.0025 | 292.963 | 18.21068548 |
| | 25 | 2175.728 | 9.004 | 3.048 | 25.0371 | 293.31 | 22.69153226 |
| | 100 | 3092.168 | 12.796 | 4.325 | 99.9368 | 293.618 | 32.24798387 |
| | 1,000 | 5292.484 | 21.901 | 7.435 | 999.7076 | 292.682 | 55.19405242 |
| | 10,000 | 6332.033 | 26.203 | 8.888 | 9993.799 | 292.88 | 66.03578629 |
| | 100,000 | 7334.057 | 30.35 | 10.293 | 100006.9201 | 292.898 | 76.48689516 |
| | 200,000 | 7985.638 | 33.046 | 11.234 | 200000 | 292.391 | 83.28125 |
| | 500,000 | 9587.548 | 39.675 | 13.461 | 500000 | 292.814 | 99.98739919 |
| | 500,000 | 9578.745 | 39.638 | 13.449 | 500000 | 292.804 | 99.89415323 |
| | 760,000 | 10207.33 | 42.24 | 14.339 | 760000 | 292.698 | 106.4516129 |

TABLE A108-b

| Tfinal mm | OD mm | ID mm | Height mm | Mass g | Density g/cc |
|---|---|---|---|---|---|
| 25.40 | 217.90 | 167.10 | 733.43 | 967 | 0.086 |

TABLE A109-a

| A109 ORM Beads bulk fill | CVP (m) | Flow correct (sccm) | Qtot (W) | k (mW/m-K) | CVP (m) | WBT (K) | Q/Am (W/m2) |
|---|---|---|---|---|---|---|---|
|  | 0.005 | 946.562 | 3.917 | 1.326 | 0.005 | 293.257 | 9.871471774 |
| HV to NV | 0.005 | 894.896 | 3.703 | 1.255 | 0.0046 | 293.092 | 9.332157258 |
|  | 0.005 | 944.996 | 3.911 | 1.32 | 0.003 | 293.938 | 9.856350806 |
|  | 1 | 1033.533 | 4.277 | 1.447 | 0.9998 | 293.355 | 10.77872984 |
|  | 10 | 1496.822 | 6.194 | 2.099 | 9.9278 | 293.119 | 15.60987903 |
|  | 100 | 3242.139 | 13.416 | 4.554 | 100.076 | 292.74 | 33.81048387 |
|  | 100 | 3288.488 | 13.608 | 4.612 | 99.9742 | 293.042 | 34.29435484 |
|  | 1,000 | 5486.875 | 22.706 | 7.692 | 1000.2033 | 293.147 | 57.22278226 |
|  | 10,000 | 6573.075 | 27.2 | 9.216 | 10000.38 | 293.104 | 68.5483871 |
|  | 100,000 | 7465.183 | 30.892 | 10.46 | 100033.4264 | 293.254 | 77.85282258 |
|  | 100,000 | 7461.727 | 30.878 | 10.464 | 100029.3308 | 293.073 | 77.81754032 |
|  | 760,000 | 9091.834 | 27.623 | 12.756 | 760000 | 292.97 | 69.61441532 |

TABLE A109-b

| Tfinal mm | OD mm | ID mm | Height mm | Mass g | Density g/cc |
|---|---|---|---|---|---|
| 25.40 | 217.90 | 167.10 | 774.70 | 1201 | 0.101 |

TABLE A110-a

| A110 LCI#1 blanket | CVP (m) | Flow correct (sccm) | Qtot (W) | k (mW/m-K) | CVP (m) | WBT (K) | Q/Am (W/m2) |
|---|---|---|---|---|---|---|---|
|  | 0.002 | 205.848 | 0.852 | 0.253 | 0.002 | 292.953 | 2.487346975 |
| HV to NV | 0.1 | 301.01 | 1.246 | 0.369 | 0.1035 | 293.179 | 3.63759898 |
|  | 1 | 414.435 | 1.715 | 0.509 | 0.9888 | 292.946 | 5.006807584 |
|  | 10 | 1077.521 | 4.459 | 1.326 | 10.0039 | 292.38 | 13.01769972 |
|  | 100 | 2653.854 | 10.982 | 3.257 | 100.0035 | 293.017 | 32.06108507 |
|  | 1,000 | 4181.252 | 17.303 | 5.133 | 991.5724 | 292.969 | 50.51474731 |
|  | 10,000 | 5142.219 | 21.296 | 6.316 | 9989.515 | 293.011 | 62.17199668 |
|  | 100,000 | 7303.403 | 30.223 | 8.962 | 99836 | 293.051 | 88.23367091 |
|  | 760,000 | 10791.607 | 44.657 | 13.272 | 768390.9742 | 292.58 | 130.3725984 |

TABLE A110-b

| Tfinal mm | OD mm | ID mm | Height mm | Mass g | Density g/cc |
|---|---|---|---|---|---|
| 21.86 | 210.83 | 167.10 |  |  |  |

TABLE A111-a

| A111 Layered aerogel-Pblanket | CVP (m) | Flow correct (sccm) | Qtot (W) | k (mW/m-K) | CVP (m) | WBT (K) | Q/Am (W/m2) |
|---|---|---|---|---|---|---|---|
| 6 layers of 2 mm | 0.010 | 1601.149 | 6.626 | 1.678 | 0.01 | 292.597 | 19.69096345 |
|  | 1 | 1759.041 | 7.279 | 1.842 | 0.9888 | 292.82 | 21.63153078 |
| HV to NV | 10 | 2281.078 | 9.439 | 2.388 | 10.0069 | 292.855 | 28.05055901 |
|  | 100 | 3424.129 | 14.17 | 3.588 | 100.0189 | 292.605 | 42.11001389 |
|  | 1,000 | 5040.028 | 20.856 | 5.27 | 997.3821 | 293.09 | 61.97928368 |
|  | 1,000 | 5031.295 | 20.82 | 5.259 | 999.6162 | 293.149 | 61.87229988 |
|  | 10,000 | 6518.375 | 26.974 | 6.82 | 10002.9041 | 292.966 | 80.16058678 |
|  | 100,000 | 8887.418 | 36.778 | 9.292 | 99986.7348 | 293.107 | 109.2958427 |
|  | 100,000 | 8992.79 | 37.214 | 9.407 | 99878.6095 | 293.003 | 110.5915354 |
|  | 760,000 | 12712.59 | 52.607 | 13.266 | 760000 | 293.516 | 156.3360269 |
|  | 760,000 | 12707.493 | 52.586 | 13.29 | 760000 | 293.044 | 156.2736197 |

-continued

TABLE A111-b

| Tfinal mm | OD mm | ID mm | Height mm | Mass g | Density g/cc | Density layers/mm |
|---|---|---|---|---|---|---|
| 18.28 | 203.67 | 167.10 | | | | 0.328 |

TABLE A112-a

| A112 Layered aerogel-Cblanket | CVP (m) | Flow correct (sccm) | Qtot (W) | k (mW/m-K) | CVP (m) | WBT (K) | Q/Am (W/m2) |
|---|---|---|---|---|---|---|---|
| 2 layers of 10 mm | 0.005 | 1159.99 | 4.8 | 1.468 | 0.005 | 292.973 | 13.96087068 |
| | 1 | 1299.283 | 5.377 | 1.643 | 1.0046 | 293.205 | 15.63908367 |
| HV to NV | 10 | 1626.072 | 6.729 | 2.061 | 9.9805 | 292.691 | 19.57139558 |
| | 100 | 2299.153 | 9.514 | 2.913 | 99.084 | 292.74 | 27.67160909 |
| | 1,000 | 3367.119 | 13.934 | 4.261 | 997.6043 | 293.009 | 40.52724417 |
| | 10,000 | 4426.682 | 18.318 | 5.603 | 9996.5616 | 292.96 | 53.27817273 |
| | 100,000 | 5327.628 | 22.047 | 6.754 | 100364.771 | 292.612 | 64.12402413 |
| | 760,000 | 8916.253 | 36.897 | 11.277 | 766352.8372 | 293.121 | 107.3154678 |
| | 760,000 | 8893.504 | 36.803 | 11.235 | 767571.949 | 293.378 | 107.0420674 |

TABLE A112-b

| Tfinal mm | OD mm | ID mm | Height mm | Mass g | Density g/cc | Density layers/mm |
|---|---|---|---|---|---|---|
| 22.66 | 212.42 | 167.10 | | | 0.133 | 0.088 |

TABLE A113-a

| A113 Cg + 15 MLI blanket | CVP (m) | Flow correct (sccm) | Qtot (W) | k (mW/m-K) | CVP (m) | WBT (K) | Q/Am (W/m2) |
|---|---|---|---|---|---|---|---|
| 1 + 15 layers mli | 0.003 | 108.987 | 0.451 | 0.132 | 0.003 | 292.866 | 1.318309402 |
| | 0.1 | 133.083 | 0.551 | 0.162 | 0.1 | 292.421 | 1.610617473 |
| HV to NV | 1 | 214.645 | 0.888 | 0.261 | 1.002 | 293.131 | 2.595695674 |
| | 10 | 674.879 | 2.793 | 0.821 | 9.9886 | 292.802 | 8.164164433 |
| | 100 | 2371.324 | 9.813 | 2.881 | 99.9354 | 292.95 | 28.68419104 |
| | 1,000 | 4516.819 | 18.691 | 5.49 | 982.1647 | 292.868 | 54.63530162 |
| | 10,000 | 6173.64 | 25.548 | 7.492 | 9952.0672 | 293.192 | 74.67886607 |
| | 10,000 | 6070.234 | 25.12 | 7.358 | 10051.2977 | 293.456 | 73.42778753 |
| | 100,000 | 8112.506 | 33.571 | 9.884 | 99925.0627 | 292.349 | 98.13074264 |
| | 760,000 | 11387.704 | 47.124 | 13.906 | 760000 | 291.872 | 137.7472555 |
| | 760,000 | 11251.869 | 46.562 | 13.722 | 760000 | 292.144 | 136.1044842 |

TABLE A113-b

| Tfinal mm | OD mm | ID mm | Height mm | Mass g | Density g/cc | Density layers/mm |
|---|---|---|---|---|---|---|
| 21.55 | 210.19 | 167.10 | | | | |

TABLE A114-a

| A114 Vacuum Only | CVP (m) | Flow correct (sccm) | Qtot (W) | k (mW/m-K) | CVP (m) | WBT (K) | Q/Am (W/m2) |
|---|---|---|---|---|---|---|---|
| Vacuum space in Black Sleeve | 0.003 | 7446.863 | 30.816 | 10.443 | 0.003 | 293.063 | 88.42396626 |
| | 0.01 | 7496.978 | 31.024 | 10.524 | 0.02 | 292.845 | 89.02080508 |

-continued

| | | | | | | | |
|---|---|---|---|---|---|---|---|
| HV to SV | 0.01 | 7619.989 | 31.533 | 10.694 | 0.02 | 292.913 | 90.48133853 |
| | 0.01 | 7662.417 | 31.708 | 10.767 | 0.02 | 292.643 | 90.98348657 |
| | 1 | 8917.153 | 36.901 | 12.52 | 0.9919 | 292.805 | 105.8843711 |
| | 1 | 8911.606 | 36.878 | 12.566 | 1.0119 | 291.891 | 105.8183745 |
| | 10 | 12906.754 | 53.41 | 18.159 | 10.0011 | 292.363 | 153.2555827 |
| | 100 | 15960.741 | 66.048 | 22.441 | 99.9876 | 292.508 | 189.5192797 |

TABLE A114-b

| Tfinal mm | OD mm | ID mm | Height mm | Mass g | Density g/cc |
|---|---|---|---|---|---|
| 25.40 | 217.90 | 167.10 | | | |

TABLE A115-a

| A115 Blk Granules | CVP (m) | Flow correct (sccm) | Qtot (W) | k (mW/m-K) | CVP (m) | WBT (K) | Q/Am (W/m2) |
|---|---|---|---|---|---|---|---|
| Opacified Aerogel Granules | 0.001 | 1109.161 | 4.59 | 1.561 | 0.003 | 292.352 | 13.17062582 |
| | 0.001 | 1136.298 | 4.702 | 1.59 | 0.003 | 293.549 | 13.49200056 |
| HV to SV | 0.001 | 1130.137 | 4.677 | 1.582 | 0.003 | 293.43 | 13.42026513 |
| | 0.1 | 1151.105 | 4.763 | 1.614 | 0.1011 | 293.1 | 13.66703502 |
| | 1 | 1198.457 | 4.959 | 1.679 | 0.9998 | 293.26 | 14.22944083 |
| | 10 | 1781.07 | 7.37 | 2.494 | 9.9927 | 293.398 | 21.14760616 |
| | 10 | 1811.694 | 7.497 | 2.541 | 10.0017 | 293.061 | 21.51202217 |
| | 100 | 3620.854 | 14.984 | 5.074 | 100.0839 | 293.216 | 42.99535016 |
| | 1,000 | 5805.77 | 24.025 | 8.134 | 974.054 | 293.263 | 68.93775277 |
| | 1,000 | 5793.835 | 23.976 | 8.124 | 990.3113 | 293.09 | 68.79715132 |
| | 10,000 | 6702.525 | 27.736 | 9.399 | 9855.0051 | 293.081 | 79.5861607 |
| | 100,000 | 7383.134 | 30.553 | 10.369 | 99879.5657 | 292.754 | 87.66930949 |
| | 100,000 | 7453.672 | 30.845 | 10.439 | 99523.9492 | 293.345 | 88.50717936 |
| | 760,000 | 10285.612 | 42.564 | 14.413 | 760652.1381 | 293.233 | 122.1338817 |
| | 760,000 | 10275.62 | 42.522 | 14.415 | 759799.8192 | 292.996 | 122.0133662 |

TABLE A115-b

| Tfinal mm | OD mm | ID mm | Height mm | Mass g | Density g/cc |
|---|---|---|---|---|---|
| 25.40 | 217.90 | 167.10 | 742.95 | 934.095 | 0.082 |

TABLE A116-a

| A116 Stky Beads clam-shell | CVP (m) | Flow correct (sccm) | Qtot (W) | k (mW/m-K) | CVP (m) | WBT (K) | Q/Am (W/m2) |
|---|---|---|---|---|---|---|---|
| Black Beads & Binder | 0.001 | 1858.903 | 7.692 | 2.671 | 0.003 | 292.648 | 22.00200718 |
| | 0.001 | 1788.474 | 7.401 | 2.565 | 0.003 | 293.079 | 21.16963795 |
| HV to NV | 0.001 | 1856.464 | 7.682 | 2.663 | 0.003 | 293.07 | 21.97340343 |
| | 10 | 2632.427 | 10.893 | 3.774 | 10.9765 | 293.185 | 31.15806867 |
| | 10 | 2540.394 | 10.513 | 3.644 | 10.9064 | 293.05 | 30.07112604 |
| | 100 | 4686.1 | 19.392 | 6.722 | 100.9624 | 293.029 | 55.46839876 |
| | 100 | 4699.582 | 19.449 | 6.741 | 100.1498 | 293.079 | 55.63144015 |
| | 1,000 | 7884.332 | 32.627 | 11.311 | 998.5848 | 293.019 | 93.3254665 |
| | 1,000 | 7683.614 | 31.796 | 11.019 | 1004.4207 | 293.105 | 90.94849458 |
| | 10,000 | 9291.155 | 38.448 | 13.321 | 10114.298 | 293.156 | 109.9757114 |
| | 10,000 | 9301.996 | 38.493 | 13.342 | 10150.8743 | 293.063 | 110.1044283 |
| | 100,000 | 10053.696 | 41.604 | 14.439 | 99105.8242 | 292.783 | 119.003056 |
| | 100,000 | 9935.936 | 41.117 | 14.25 | 99056.205 | 293.087 | 117.6100532 |
| | 760,000 | 13573.026 | 56.167 | 19.39 | 760000 | 293.928 | 160.6587022 |
| | 760,000 | 18980.653 | 78.545 | 27.334 | 760000 | 292.202 | 224.6681817 |
| | 760,000 | 18918.323 | 78.287 | 27.375 | 760000 | 291.179 | 223.9302049 |
| | 760,000 | 19767.274 | 81.8 | 28.299 | 760000 | 293.47 | 233.9787035 |

TABLE A116-b

| Tfinal mm | OD mm | ID mm | Height mm | Mass g | Density g/cc |
|---|---|---|---|---|---|
| 26.07 | 217.99 | 165.86 | 647.70 | 1228 | 0.121 |

TABLE A117-a

| A117 aerogel-CO2 blanket | CVP (m) | Flow correct (sccm) | Qtot (W) | k (mW/m-K) | CVP (m) | WBT (K) | Q/Am (W/m2) |
|---|---|---|---|---|---|---|---|
| 7 layers of 10 mm | 760000 | 6297.671 | 26.061 | 20.26 | 757138.5419 | 292.943 | 62.21187262 |
| | 100000 | 2449.727 | 10.137 | 7.876 | 99546.1569 | 293.099 | 24.19867821 |
| NV to SV | 10000 | 2014.502 | 8.336 | 6.478 | 9726.8662 | 293.055 | 19.89939642 |
| | 10000 | 1993.009 | 8.247 | 6.404 | 9720.2925 | 293.217 | 19.68693886 |
| | 1000 | 1713.147 | 7.089 | 5.508 | 933.0575 | 293.092 | 16.92260332 |
| | 1000 | 1734.94 | 7.179 | 5.576 | 810.1869 | 293.162 | 17.13744805 |
| | 100 | 960.857 | 3.976 | 3.098 | 99.1543 | 292.489 | 9.491362785 |
| | 100 | 980.359 | 4.057 | 3.16 | 99.1462 | 292.55 | 9.684723043 |

TABLE A117-b

| Tfinal mm | OD mm | ID mm | Height mm | Mass g | Density g/cc |
|---|---|---|---|---|---|
| 70.02 | 307.14 | 167.10 | | | |

TABLE A118-a

| A118 MLI #1 | CVP (m) | Flow correct (sccm) | Qtot (W) | k (mW/m-K) | CVP (m) | WBT (K) | Q/Am (W/m2) |
|---|---|---|---|---|---|---|---|
| 30 layers + 10 layers Mylar & paper | 0.001 | 49.335 | 0.204 | 0.053 | 0.005 | 293.198 | 0.604276532 |
| | 0.001 | 27.691 | 0.115 | 0.03 | 0.005 | 293.836 | 0.340646084 |
| | 0.001 | 30.558 | 0.126 | 0.033 | 0.005 | 293.284 | 0.373229623 |
| HV to NV | 0.05 | 44.669 | 0.185 | 0.048 | 0.0495 | 293.404 | 0.547995875 |
| | 0.1 | 41.166 | 0.17 | 0.044 | 0.0986 | 293.775 | 0.503563777 |
| | 1 | 98.888 | 0.409 | 0.107 | 0.9972 | 293.428 | 1.211515204 |
| | 10 | 431.149 | 1.784 | 0.465 | 10.0141 | 292.989 | 5.284457515 |
| | 100 | 2434.239 | 10.073 | 2.626 | 99.9882 | 293.128 | 29.83763483 |
| | 1,000 | 9317.491 | 38.557 | 10.044 | 1021.5493 | 293.254 | 114.2112267 |
| | 10,000 | 13691.248 | 56.657 | 14.775 | 10073.4206 | 293.024 | 167.8259582 |
| | 100,000 | 14112.174 | 58.398 | 15.191 | 100099.9811 | 293.567 | 172.9830437 |
| | 760,000 | 15162.13 | 62.743 | 16.356 | 768985.7143 | 293.108 | 185.8535414 |

TABLE A118-b

| Tfinal mm | OD mm | ID mm | Height mm | Mass g | Density g/cc | Density layers/mm |
|---|---|---|---|---|---|---|
| 18.95 | 204.99 | 167.10 | | | | 2.113 |

TABLE A119-a

| A119 Robust MLI #1 | CVP (m) | Flow correct (sccm) | Qtot (W) | k (mW/m-K) | CVP (m) | WBT (K) | Q/Am (W/m2) |
|---|---|---|---|---|---|---|---|
| Aerogel-P and Mylar & Paper | 0.001 | 191.604 | 0.793 | 0.177 | 0.0042 | 292.973 | 2.384355699 |
| | 0.001 | 194.145 | 0.803 | 0.179 | 0.0037 | 293.673 | 2.414423237 |
| HV to NV | 1 | 415.9 | 1.721 | 0.385 | 1.4647 | 293.018 | 5.174623151 |

-continued

| | 10 | 1586.572 | 6.565 | 1.473 | 10.0313 | 292.521 | 19.73933817 |
| | 10 | 1406.697 | 5.821 | 1.302 | 9.9513 | 293.19 | 17.5023134 |
| | 1000 | 11973.887 | 49.55 | 11.074 | 1004.245 | 293.28 | 148.9846468 |
| | 1000 | 11865.318 | 49.101 | 10.964 | 995.3252 | 293.478 | 147.6346144 |

TABLE A119-b

| Tfinal mm | OD mm | ID mm | Height mm | Mass g | Density g/cc | Density layers/mm |
|---|---|---|---|---|---|---|
| 15.97 | 199.05 | 167.10 | | | | 0.815 |

TABLE A120-a

| A120 Robust MLI #2 | CVP (m) | Flow correct (sccm) | Qtot (W) | k (mW/m-K) | CVP (m) | WBT (K) | Q/Am (W/m2) |
|---|---|---|---|---|---|---|---|
| 4 layers aerogel-C mli | 760,000 | 8269.634 | 34.221 | 13.505 | 759775.3703 | 292.215 | 96.0351825 |
| | 760,000 | 8256.118 | 24.165 | 13.422 | 759320.3544 | 293.196 | 67.8147975 |
| NV to HV | 100,000 | 4550.043 | 18.829 | 7.393 | 100210.3269 | 293.308 | 52.84025748 |
| | 100,000 | 4616.86 | 19.105 | 7.503 | 99578.622 | 293.268 | 53.61480266 |
| | 10,000 | 3269.766 | 13.531 | 5.316 | 10153.6099 | 293.169 | 37.97235775 |
| | 10,000 | 3265.983 | 13.515 | 5.304 | 10015.8976 | 293.427 | 37.92745658 |
| | 1,000 | 2553.103 | 10.565 | 4.152 | 991.9732 | 293.128 | 29.64880346 |
| | 1,000 | 2608.279 | 10.793 | 4.237 | 987.2452 | 293.371 | 30.28864512 |
| | 100 | 1704.98 | 7.055 | 2.774 | 100.7945 | 292.987 | 19.79860941 |
| | 100 | 1723.33 | 7.131 | 2.804 | 100.8585 | 292.998 | 20.01188996 |
| | 10 | 912.796 | 3.777 | 1.483 | 10.0455 | 293.308 | 10.59948232 |
| | 10 | 876.735 | 3.628 | 1.425 | 10.0423 | 293.301 | 10.18134017 |
| | 1 | 440.447 | 1.823 | 0.716 | 1.0303 | 293.085 | 5.115926995 |
| | 1 | 431.335 | 1.785 | 0.701 | 1.0323 | 293.274 | 5.009286718 |
| | 0.01 | 312.378 | 1.293 | 0.507 | 0.0662 | 293.527 | 3.628575757 |
| | 0.01 | 302.877 | 1.253 | 0.492 | 0.0089 | 293.281 | 3.516322833 |

TABLE A120-b

| Tfinal mm | OD mm | ID mm | Height mm | Mass g | Density g/cc | Density layers/mm |
|---|---|---|---|---|---|---|
| 30.14 | 227.38 | 167.10 | | | | 7.398 |

TABLE A121-a

| A121 Robust MLI #3 | CVP (m) | Flow correct (sccm) | Qtot (W) | k (mW/m-K) | CVP (m) | WBT (K) | Q/Am (W/m2) |
|---|---|---|---|---|---|---|---|
| 5 layers aerogel-P + 20 layers mli | 0.01 | 23.979 | 0.099 | 0.028 | 0.0109 | 295.229 | 0.290479001 |
| | 1 | 87.205 | 0.361 | 0.103 | 0.9866 | 293.115 | 1.059221406 |
| HV to NV | 10 | 479.328 | 1.984 | 0.563 | 10.1304 | 293.197 | 5.821316537 |
| | 100 | 2719.511 | 11.254 | 3.198 | 99.1682 | 293.033 | 33.02071386 |
| | 1,000 | 7398.427 | 30.616 | 8.769 | 1019.9431 | 291.364 | 89.83136446 |
| | 10,000 | 9779.1 | 40.468 | 11.909 | 9934.4319 | 285.671 | 118.7384262 |
| | 100,000 | 12412.202 | 51.364 | 15.068 | 100199.188 | 286.318 | 150.7087211 |
| | 760,000 | 15565.729 | 64.414 | 19.302 | 767478.8256 | 281.937 | 188.9991348 |

TABLE A121-b

| Tfinal mm | OD mm | ID mm | Height mm | Mass g | Density g/cc | Density layers/mm |
|---|---|---|---|---|---|---|
| 20.75 | 208.60 | 167.10 | | | | |

TABLE A122-a

A122 JSC-1A Lunar Simulant

| | CVP (m) | Flow correct (sccm) | Qtot (W) | k (mW/m-K) | CVP (m) | WBT (K) | Q/Am (W/m2) |
|---|---|---|---|---|---|---|---|
| | 0.01 | 671.238 | 2.778 | 0.955 | 0.0107 | 293.222 | 7.954794283 |
| | 0.005 | 675.383 | 2.795 | 0.961 | 0.0087 | 293.19 | 8.00347373 |
| HV to NV | 10 | 835.907 | 3.459 | 1.188 | 10.0021 | 293.446 | 9.904835646 |
| | 10 | 836.823 | 3.463 | 1.189 | 10.0037 | 293.457 | 9.916289633 |
| | 100 | 1855.467 | 7.678 | 2.636 | 100.0069 | 293.49 | 21.98592891 |
| | 100 | 1906.934 | 7.891 | 2.71 | 100.079 | 293.414 | 22.59585374 |
| | 1,000 | 8831.716 | 36.547 | 12.488 | 957.9103 | 294.537 | 104.6522198 |
| | 1,000 | 8764.674 | 36.27 | 12.424 | 996.833 | 293.991 | 103.8590312 |
| | 760,000 | 32333.873 | 133.803 | 48.827 | 766640.3717 | 280.758 | 383.1444706 |

TABLE A122-b

| Tfinal mm | OD mm | ID mm | Height mm | Mass g | Density g/cc |
|---|---|---|---|---|---|
| 25.86 | 218.81 | 167.10 | 774.70 | 20085.67 | 1.654 |

TABLE A123-a

A123 JSC-1A Lunar Simulant more dense

| | CVP (m) | Flow correct (sccm) | Qtot (W) | k (mW/m-K) | CVP (m) | WBT (K) | Q/Am (W/m2) |
|---|---|---|---|---|---|---|---|
| | 0.01 | 779.358 | 3.225 | 1.109 | 0.0142 | 293.235 | 9.23477738 |
| HV to NV | 10 | 950.236 | 3.932 | 1.352 | 9.937 | 293.187 | 11.25926966 |
| | 100 | 2255.07 | 9.332 | 3.204 | 100.838 | 293.513 | 26.72215272 |
| | 1,000 | 6772.348 | 28.025 | 9.63 | 999.5151 | 293.312 | 80.24949956 |
| | 1,000 | 6833.56 | 28.278 | 9.706 | 1000.3479 | 293.564 | 80.97396427 |
| | 10,000 | 24720.155 | 102.296 | 35.124 | 10136.873 | 293.489 | 292.924275 |

TABLE A123-b

| Tfinal mm | OD mm | ID mm | Height mm | Mass g | Density g/cc |
|---|---|---|---|---|---|
| 25.86 | 218.81 | 167.10 | 790.25 | 22170.73 | 1.790 |

TABLE A124-a

A124 JSC-1A Lunar Simulant most dense

| | CVP (m) | Flow correct (sccm) | Qtot (W) | k (mW/m-K) | CVP (m) | WBT (K) | Q/Am (W/m2) |
|---|---|---|---|---|---|---|---|
| HV to NV | 0.01 | 921.331 | 3.813 | 1.31 | 0.0094 | 293.349 | 10.91851354 |

TABLE A124-b

| Tfinal mm | OD mm | ID mm | Height mm | Mass g | Density g/cc | Density lbm/ft3 |
|---|---|---|---|---|---|---|
| 25.86 | 218.81 | 167.10 | 809.50 | 23436.42 | 1.847 | 115.303 |

TABLE A125-a

A125 MLI Baseline

| | CVP (m) | Flow correct (sccm) | Qtot (W) | k (mW/m-K) | CVP (m) | WBT (K) | Q/Am (W/m2) |
|---|---|---|---|---|---|---|---|
| 40 layers Mylar & Net | 0.01 | 31.874 | 0.132 | 0.028 | 0.0098 | 293.827 | 0.398042092 |
| | 0.01 | 34.5 | 0.143 | 0.031 | 0.0175 | 293.062 | 0.431212266 |

-continued

| | | | | | | | |
|---|---|---|---|---|---|---|---|
| HV to NV | 0.1 | 44.091 | 0.182 | 0.04 | 0.1 | 293.074 | 0.548815612 |
| | 1 | 80.507 | 0.333 | 0.072 | 1 | 292.84 | 1.004151642 |
| | 10 | 517.697 | 2.142 | 0.464 | 10.0326 | 293.278 | 6.459137586 |
| | 10 | 521.479 | 2.158 | 0.468 | 10.1426 | 292.856 | 6.507385112 |
| | 100 | 3603.543 | 14.912 | 3.238 | 100.1033 | 292.546 | 44.96669453 |
| | 1,000 | 8982.948 | 37.173 | 8.063 | 1040.1694 | 292.794 | 112.094081 |
| | 10,000 | 11340.915 | 46.931 | 10.195 | 10036.106 | 292.449 | 141.5190411 |
| | 100,000 | 16447.466 | 68.062 | 14.644 | 99101.6053 | 294.523 | 205.238946 |
| | 100,000 | 15058.176 | 62.313 | 13.501 | 99103.1878 | 293.028 | 187.9030067 |
| | 760,000 | 18712.853 | 77.437 | 16.692 | 769366.5692 | 294.127 | 233.508981 |
| | 760,000 | 19375.742 | 80.18 | 17.443 | 768584.8287 | 292.152 | 241.7804163 |
| | 760,000 | 19594.625 | 81.086 | 17.425 | 768095.1407 | 294.791 | 244.5124324 |

TABLE A125-b

| Tfinal mm | OD mm | ID mm | Height mm | Mass g | Density g/cc | Density layers/mm |
|---|---|---|---|---|---|---|
| 15.45 | 198.04 | 167.10 | | | | 2.588 |

TABLE A126

| A126 MLI Baseline | CVP (m) | Flow correct (sccm) | Qtot (W) | k (mW/m-K) | CVP (m) | WBT (K) | Q/Am (W/m2) |
|---|---|---|---|---|---|---|---|
| 40 layers Foil & Paper | 0.01 | 46.015 | 0.19 | 0.03 | 0.00134 | 294.211 | 0.586017166 |
| | 0.01 | 50.297 | 0.208 | 0.033 | 0.0042 | 293.888 | 0.641534582 |
| HV to NV | 0.05 | 57.167 | 0.237 | 0.038 | 0.05 | 294.211 | 0.730979307 |
| | 0 | 61.133 | 0.253 | 0.04 | 0.2386 | 294.098 | 0.780328121 |
| | 0 | 60.857 | 0.252 | 0.04 | 0.3013 | 293.805 | 0.77724382 |
| | 1 | 83.596 | 0.346 | 0.055 | 1.011 | 293.271 | 1.067168102 |
| | 3 | 136.15 | 0.563 | 0.09 | 2.9994 | 293.664 | 1.736461392 |
| | 10 | 341.208 | 1.412 | 0.227 | 10.0631 | 292.514 | 4.355032834 |
| | 30 | 735.931 | 3.045 | 0.491 | 29.7541 | 291.966 | 9.391696161 |
| | 100 | 1546.644 | 6.4 | 1.021 | 100.0935 | 294.097 | 19.73952559 |
| | 1,000 | 8572.981 | 35.476 | 5.653 | 955.883 | 294.313 | 109.4186578 |
| | 10,000 | 15243.398 | 63.08 | 10.089 | 10093.72 | 293.521 | 194.5576991 |
| | 100,000 | 19995.574 | 82.745 | 13.373 | 100090.625 | 292.955 | 255.2104758 |
| | 760,000 | 23857.395 | 98.726 | 15.756 | 739718.166 | 293.992 | 304.5006881 |

TABLE A126

| Tfinal mm | OD mm | ID mm | Height mm | Mass g | Density g/cc | Density layers/mm |
|---|---|---|---|---|---|---|
| 11.18 | 189.34 | 167.10 | | | | 3.602 |

TABLE A128-a

| A128 MLI Baseline | CVP (m) | Flow correct (sccm) | Qtot (W) | k (mW/m-K) | CVP (m) | WBT (K) | Q/Am (W/m2) |
|---|---|---|---|---|---|---|---|
| 80 layers Foil & Paper | 0.01 | 42.467 | 0.176 | 0.051 | 0.0025 | 292.046 | 0.51576594 |
| | 0.01 | 32.042 | 0.133 | 0.038 | 0.006 | 293.54 | 0.389754943 |
| HV to NV | 0.05 | 49.274 | 0.204 | 0.058 | 0.2 | 294.098 | 0.597819613 |
| | 0 | 46.459 | 0.192 | 0.055 | 0.25 | 293.636 | 0.562653753 |
| | 1 | 53.526 | 0.221 | 0.064 | 1.142 | 293.076 | 0.647637914 |
| | 10 | 188.42 | 0.78 | 0.223 | 10.046 | 293.955 | 2.285780872 |
| | 100 | 1214.192 | 5.025 | 1.443 | 100 | 293.024 | 14.72570369 |
| | 1,000 | 5292.785 | 21.902 | 6.302 | 1055.382 | 292.683 | 64.18355468 |
| | 10,000 | 10943.222 | 45.285 | 12.815 | 10010.634 | 293.387 | 132.7071625 |
| | 100,000 | 13013.439 | 53.852 | 15.459 | 99319.897 | 293.187 | 157.8126558 |
| | 760,000 | 16548.125 | 68.479 | 19.791 | 764308.587 | 291.72 | 200.6769081 |

TABLE A128-b

| Tfinal mm | OD mm | ID mm | Height mm | Mass g | Density g/cc | Density layers/mm |
|---|---|---|---|---|---|---|
| 21.10 | 209.30 | 167.10 | | | | 3.800 |

TABLE A129-a

| A129 aerogel clam-shell pack | CVP (m) | Flow correct (sccm) | Qtot (W) | k (mW/m-K) | CVP (m) | WBT (K) | Q/Am (W/m2) |
|---|---|---|---|---|---|---|---|
| Medium load | 0.014 | 1127.316 | 4.665 | 2.0 | 0.048 | 293.652 | 12.9179786 |
| | 10 | 1787.669 | 7.398 | 3.1 | 10 | 293.664 | 20.48600336 |
| HV to NV | 100 | 2430.85 | 10.59 | 4.3 | 99 | 293.507 | 29.32505753 |
| | 1,000 | 3481.098 | 14.405 | 6.1 | 1,070 | 293.599 | 39.88927797 |
| | 760,000 | 8646.049 | 35.779 | 15.2 | 761,530 | 293.435 | 99.07660372 |

TABLE A129-b

| Tfinal mm | OD mm | ID mm | Height mm | Mass g | Density g/cc | Density layers/mm |
|---|---|---|---|---|---|---|
| 33.00 | 233.00 | 167.10 | | | | |

TABLE A130-a

| A130 aerogel clam-shell pack | CVP (m) | Flow correct (sccm) | Qtot (W) | k (mW/m-K) | CVP (m) | WBT (K) | Q/Am (W/m2) |
|---|---|---|---|---|---|---|---|
| Low load | 0.05 | 1051.651 | 4.352 | 2.0 | 0.025 | 293.419 | 11.85856885 |
| | 10 | 1371.128 | 5.674 | 2.6 | 10 | 293.519 | 15.46082713 |
| HV to NV | 100 | 2149.081 | 8.893 | 4.1 | 99 | 293.523 | 24.23213529 |
| | 1,000 | 3260.388 | 13.492 | 6.3 | 1,050 | 293.481 | 36.76374332 |
| | 10,000 | 4012.906 | 16.606 | 7.7 | 9,976 | 293.199 | 45.24894172 |
| | 100,000 | 4581.429 | 18.959 | 8.808 | 99,247 | 292.94 | 51.66052547 |
| | 760,000 | 9215.471 | 38.135 | 17.688 | 764,338 | 293.307 | 103.9123445 |
| | 760,000 | 9393.258 | 38.871 | 18.051 | 765,545 | 293.046 | 105.9178377 |

TABLE A130-b

| Tfinal mm | OD mm | ID mm | Height mm | Mass g | Density g/cc |
|---|---|---|---|---|---|
| 36.65 | 240.43 | 167.10 | | | |

TABLE A132-a

| A132 MLI Spiral Wrap | CVP (m) | Flow correct (sccm) | Qtot (W) | k (mW/m-K) | CVP (m) | WBT (K) | Q/Am (W/m2) |
|---|---|---|---|---|---|---|---|
| 40 layers Foil & Paper | 0.01 | 72.698 | 0.301 | 0.073 | 0.0065 | 293.649 | 0.897977411 |
| | 0.01 | 78.177 | 0.324 | 0.079 | 0.008 | 293.38 | 0.966593625 |
| HV to NV | 0.1 | 95.626 | 0.396 | 0.096 | 0.25 | 293.101 | 1.181392209 |
| | 1 | 149.919 | 0.62 | 0.15 | 1.146 | 294.143 | 1.849654468 |
| | 10 | 433.416 | 1.764 | 0.435 | 10.084 | 293.742 | 5.262565293 |
| | 100 | 2127.193 | 8.803 | 2.139 | 99.079 | 293.189 | 26.26211013 |

TABLE A132-b

| Tfinal mm | OD mm | ID mm | Height mm | Mass 9 | Density g/cc | Density layers/mm |
|---|---|---|---|---|---|---|
| 17.47 | 202.07 | 167.13 | | | | 2.290 |

Figure 9:
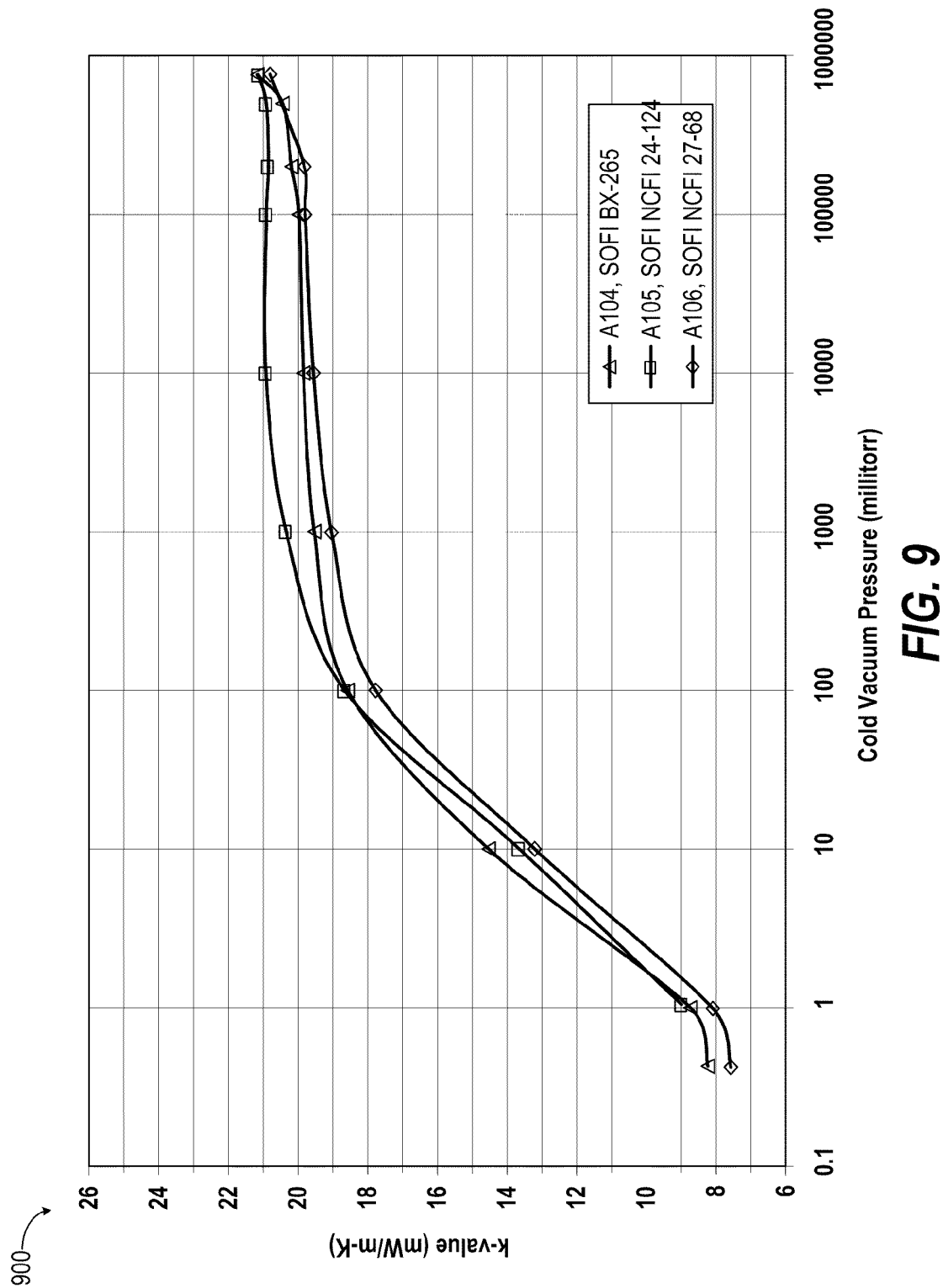
FIG. 9 illustrates a graphical plot for test results for k-value as a function of Cold Vacuum Pressure (CVP).
Figure 10:
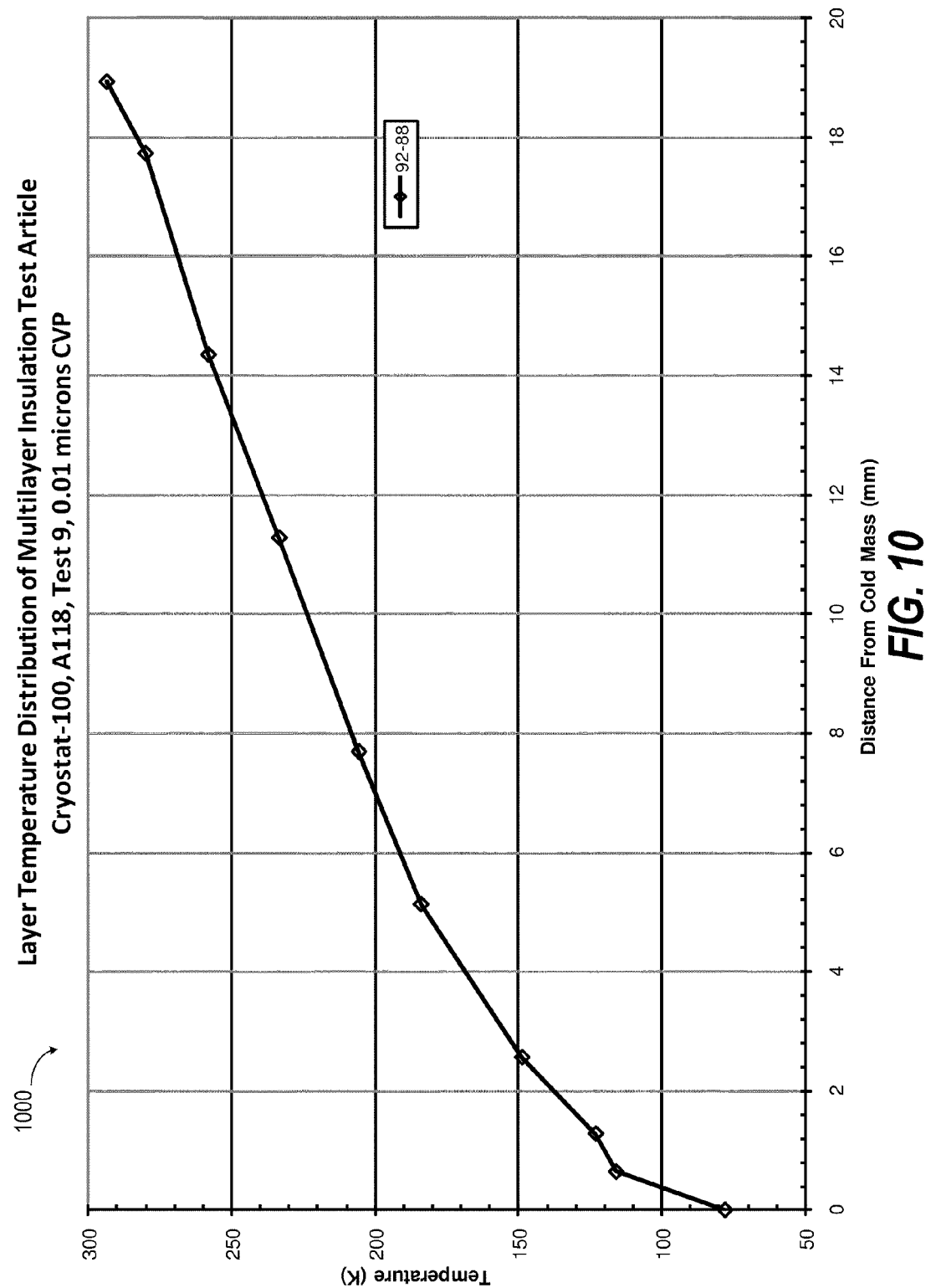
FIG. 10 illustrates a graphical plot for layer temperature distribution of multilayer insulation test article as a function of distance.
Figure 11:
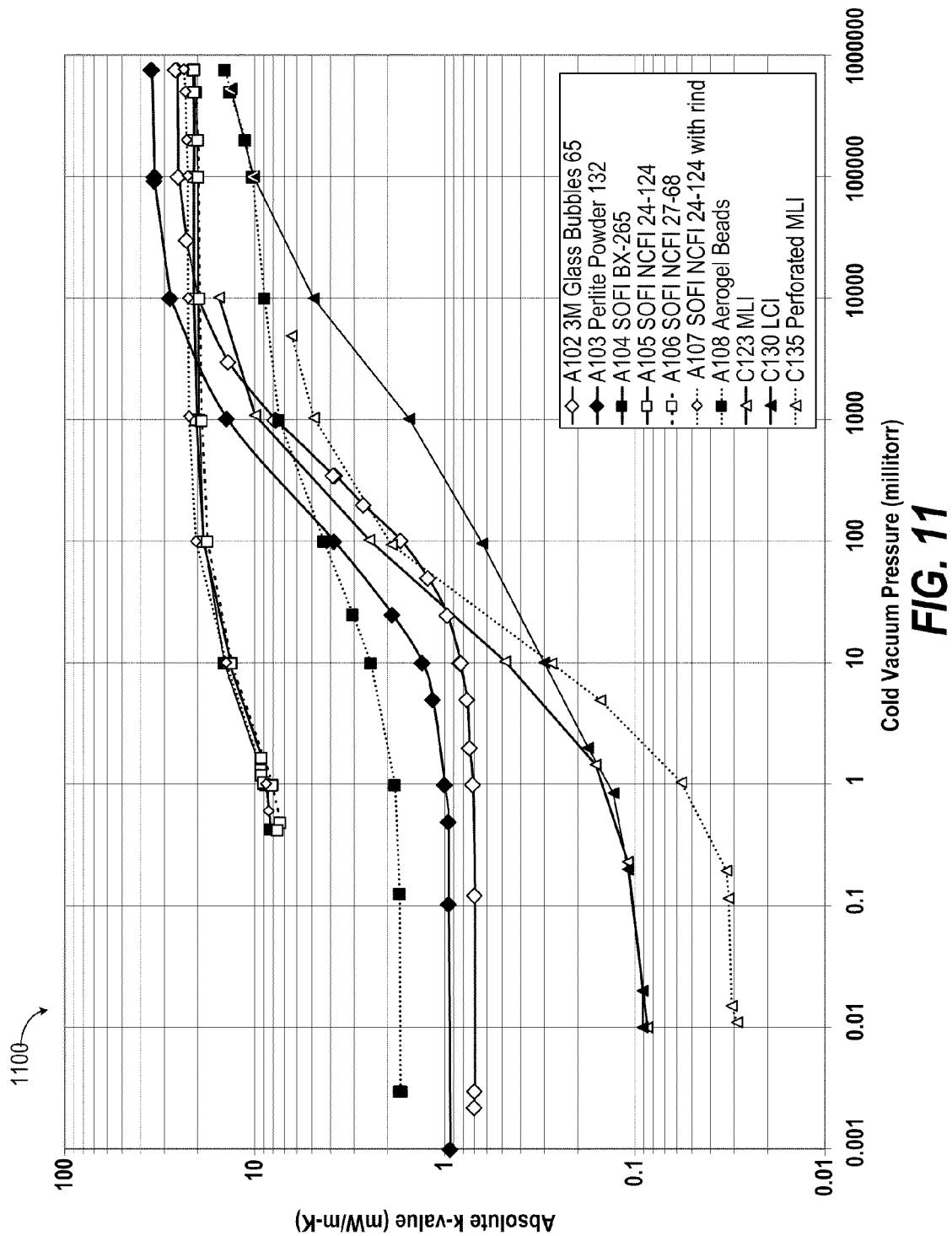
FIG. 11 illustrates a graphical plot for test results for k-value for ten specimens as a function of CVP.

Foam test specimen installation was by fitting around cold mass, using band clamps to compress slightly and eliminate seam gap for clam shell articles. Test results for k-value as a function of CVP are depicted at 900 in FIG. 9. Layer temperature distribution of a multilayer insulation test article is depicted at 1000 in FIG. 10. Test results for absolute k-value for ten specimens as a function of CVP is depicted at 1100 in FIG. 11.

Figure 12:
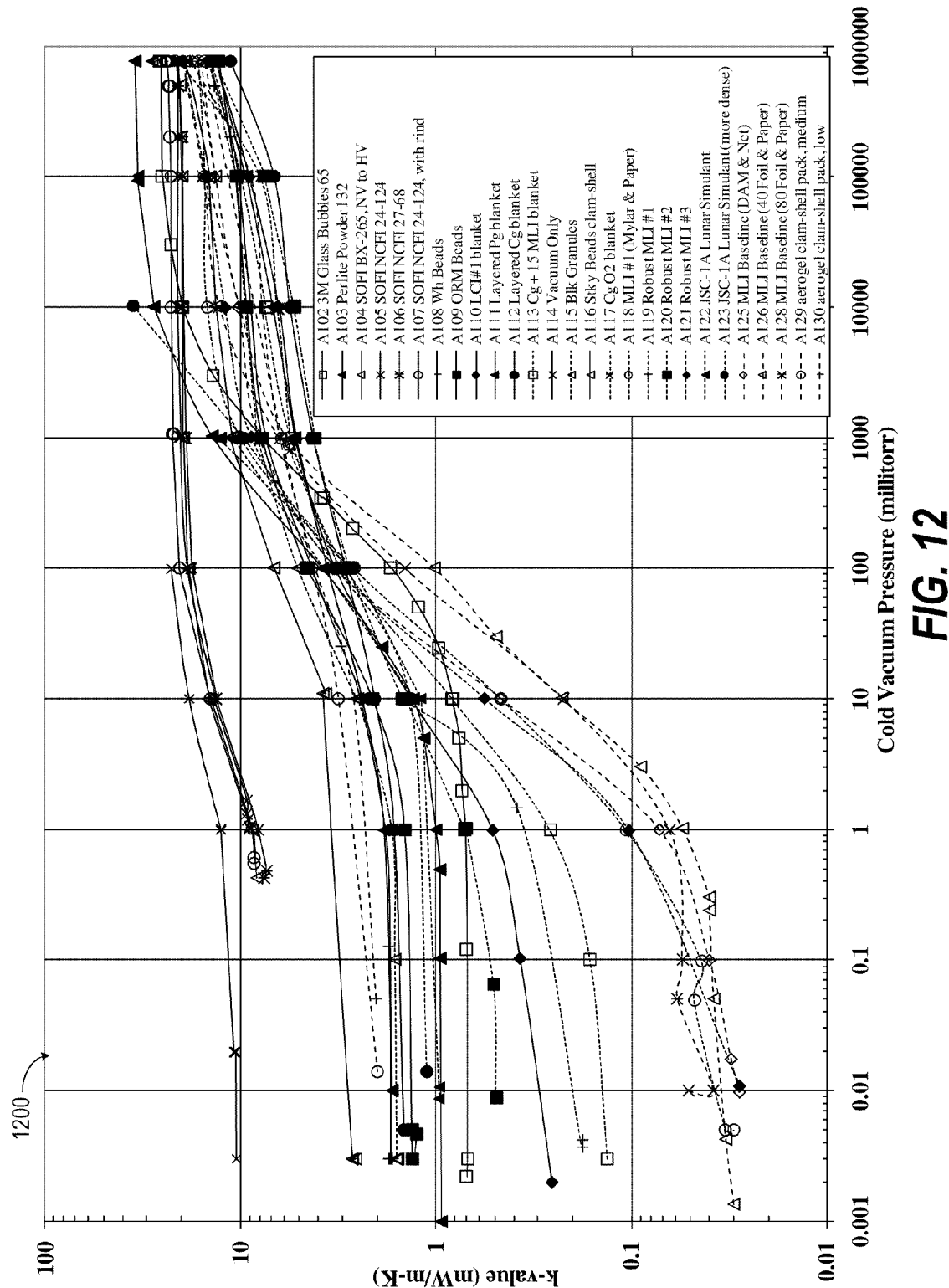
FIG. 12 illustrates a graphical chart for a wide range of empirical data obtained by the present invention.

In analyzing foam performance, the following were used
No vacuum: 21 mW/m-K
High vacuum: 7.6 mW/m-K
Multiple tests at each CVP
k-value standard deviation <1 mW/m-K
Uncertainty Analysis of Cryostat-100: <3% error In FIG. 12, a chart 1200 depicts a wide range of empirical data showing how efficient the disclosed invention is for producing high quality thermal conductivity data. Specific empirical data runs are provided in TABLE 3.

TABLE 3

| Comp | Specimen | Form | Material |
|---|---|---|---|
| A102 | 3M Glass Bubbles 65 | Bulk fill | Glass Bubbles |
| A103 | Perlite Power 132 | Bulk fill | Perlite |
| A104 | SOFI BX-265, NV to HV | Clam shell | Foam |
| A105 | SOFI NCFI 24-124 | Clam shell | Foam |
| A106 | SOFI NCFI 27-68 | Clam shell | Foam |
| A107 | SOFI NCFI 24-124, with rind | Clam shell | Foam |
| A108 | Ng Beads | Bulk fill | Perlite |
| A109 | Or Beads | Bulk fill | Aerogel |
| A110 | LCI#1 (Pyrogel, Cryogel, Cryolam) | layered | Aerogel/MLI |
| A111 | Layered Pyrogel | blanket | Aerogel |
| A112 | Layered Cryogel | Layered | Aerogel |
| A113 | Cryogel + 15 MLI (Foil & Paper) | Layered | Aerogel |
| A114 | Vacuum Only | | |
| A115 | Black Ng Granules | Bulk fill | Aerogel |
| A116 | Stky Beads | Clam shell | Aerogel |
| A117 | Cg O2 | Blanket | Aerogel |
| A118 | MLI #1 (Mylar & Paper) | layered | MLI |
| A119 | Robust MLI #1 (PS & MP) | layered | MLI |
| A120 | Robust MLI #2 (CZ & MP) | layered | MLI |
| A121 | Robust MLI #3 (PT + MP) | layered | MLI |
| A122 | JSC-1A Lunar Simulant | Bulk fill | Regolith |
| A123 | JSC-1A Lunar Simulant (more dense) | Bulk fill | Regolith |
| A124 | JSC-1A Lunar Simulant (most dense) | Bulk fill | Regolith |
| A125 | MLI Baseline (DAM & Dacron Net) | layered | MLI |
| A126 | MLI Baseline (40 Foil & Paper) | layered | MLI |
| A128 | MLI Baseline (80 Foil & Paper) | layered | MLI |
| A129 | NPack#1, medium | Clam shell | Aerogel |
| A130 | NPack #2, low | Clam shell | Aerogel |

Figure 13:
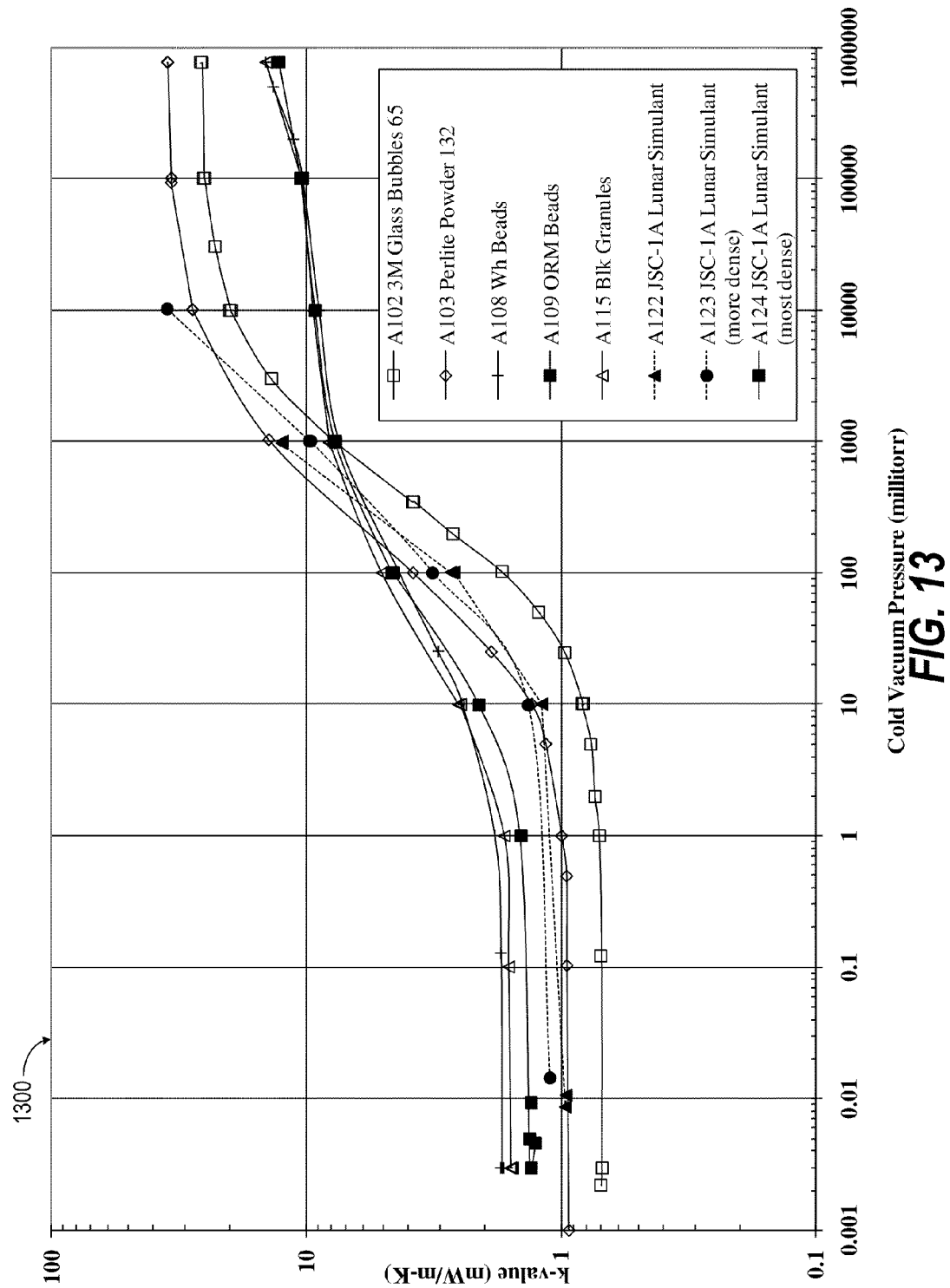
FIG. 13 illustrates a graphical chart for empirical data for powder insulation.

In FIG. 13, a chart 1300 is provided for bulk-fill or powder insulation, demonstrating that the Cryostat-100 apparatus 100 can handle all different types of materials. The specific specimens plotted are provided in TABLE 4.

TABLE 4

| Comp | Specimen | Form | Material |
|---|---|---|---|
| A102 | Glass Bubbles | Bulk fill | Glass Bubbles |
| A103 | Perlite Power | Bulk fill | Perlite |
| A108 | Aerogel I Beads white | Bulk fill | Aerogel |
| A109 | OR Beads | Bulk fill | Aerogel |
| A114 | Vacuum Only | n/a | n/a |
| A115 | Aerogel Granules black | Bulk fill | Aerogel |
| A122 | JSC-1A Lunar Simulant | Bulk fill | simulant |
| A123 | JSC-1A Lunar Simulant (more dense) | Bulk fill | simulant |
| A124 | JSC-1A Lunar Simulant (most dense) | Bulk fill | simulant |

Figure 14:
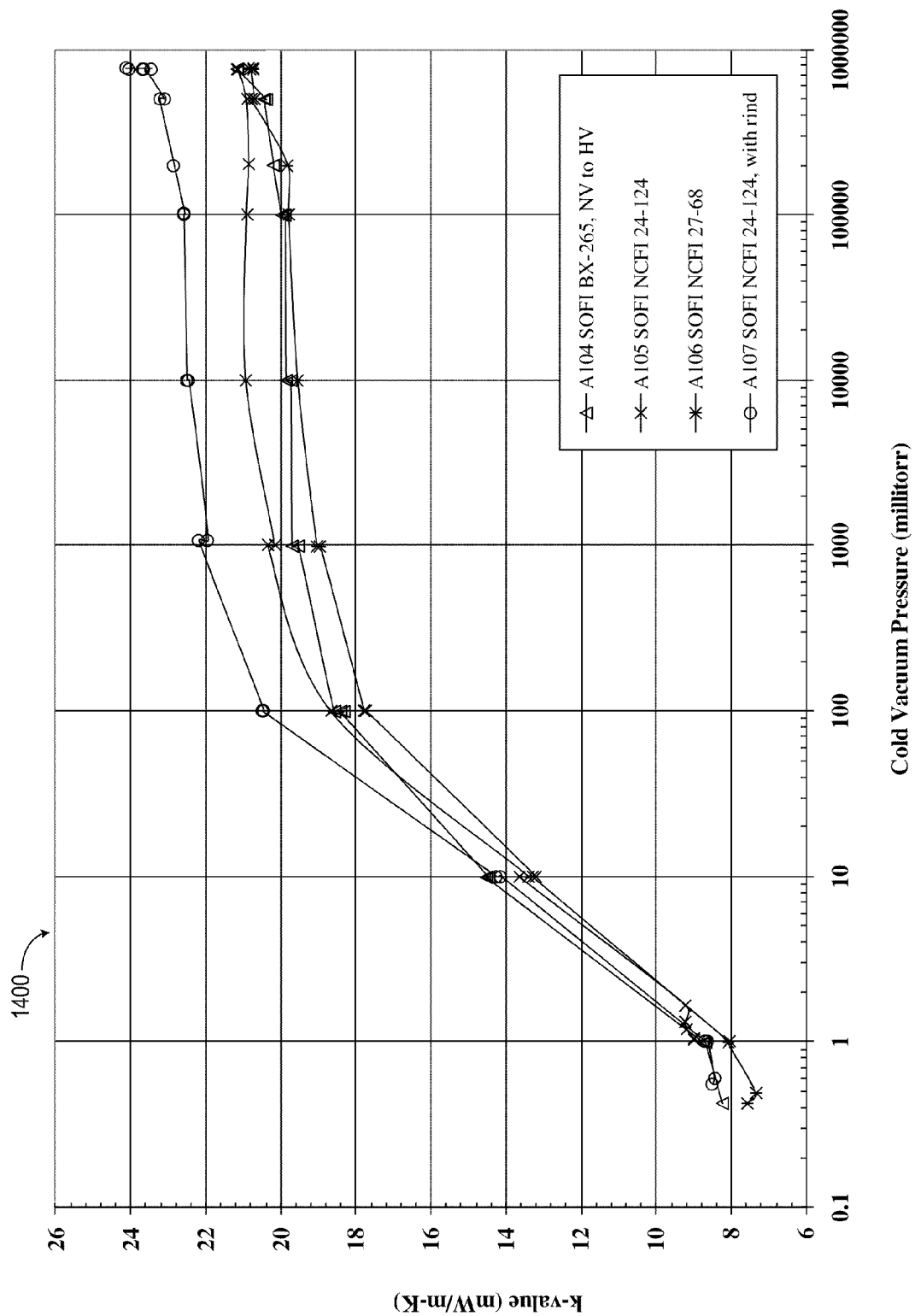
FIG. 14 illustrates a graphical chart for empirical data for foam insulation.

In FIG. 14, a chart 1400 is provided for foam insulation, demonstrating performance by the Cryostat-100 apparatus 100 more closely for non-vacuum, ambient pressure range. The specific specimens plotted are provided in TABLE 5.

TABLE 5

| Comp | Specimen | Form | Material |
|---|---|---|---|
| A104 | SOFI BX-265, NV to HV | Clam-shell | Foam |
| A105 | SOFI NCFI 24-124 | Clam-shell | Foam |
| A106 | SOFI NCFI 27-68 | Clam-shell | Foam |
| A107 | SOFI NCFI 24-124, with rind | Clam-shell | Foam |

Figure 15:
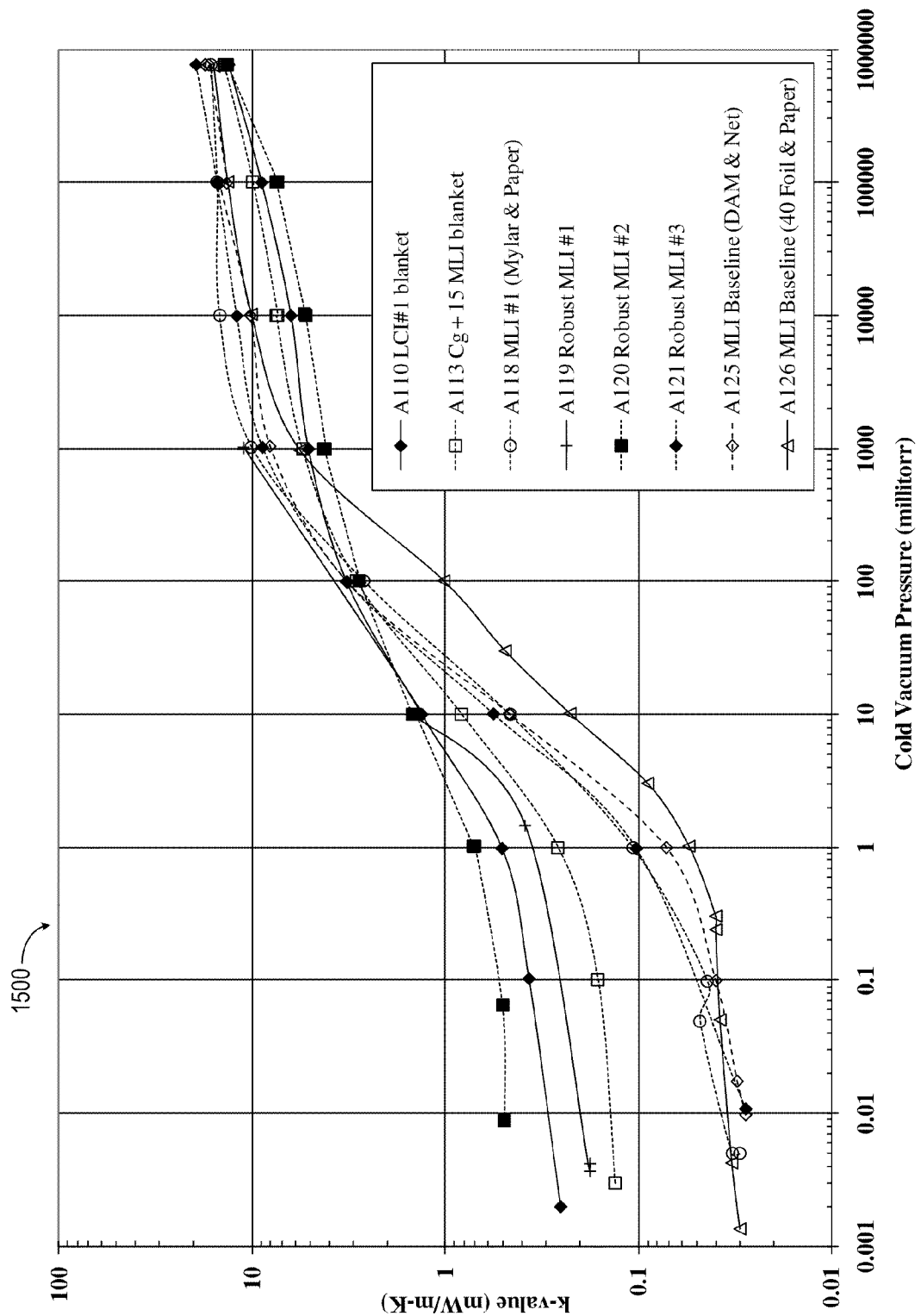
FIG. 15 illustrates a graphical chart for empirical data for Multiple Layer Insulation (MLI) and blanket insulation.

In FIG. 15, a chart 1500 is provided for MLI, blanket form insulation, demonstrating performance by the Cryostat-100 apparatus 100 for the highest performance insulation systems in the world. The specific specimens plotted are provided in TABLE 6.

TABLE 6

| Comp | Specimen | Form | Material |
|---|---|---|---|
| A110 | LCI#1 (Pyrogel, Cryogel, Cryolam) | Blanket | Aerogel/MLI |
| A113 | Cryogel + 15 MLI (Foil & Paper) | Blanket | Aerogel/MLI |
| A118 | MLI #1 (Mylar & Paper) | Blanket | MLI |
| A119 | Robust MLI #1 (PS & MP) | Blanket | Aerogel/MLI |
| A120 | Robust MLI #2 (CZ & MP) | Blanket | Aerogel/MLI |
| A121 | Robust MLI #3 (PT + MP) | Blanket | Aerogel/MLI |
| A125 | MLI Baseline (DAM & Dacron Net) | Blanket | MLI |
| A126 | MLI Baseline (40 Foil & Paper) | Blanket | MLI |

Figure 16:
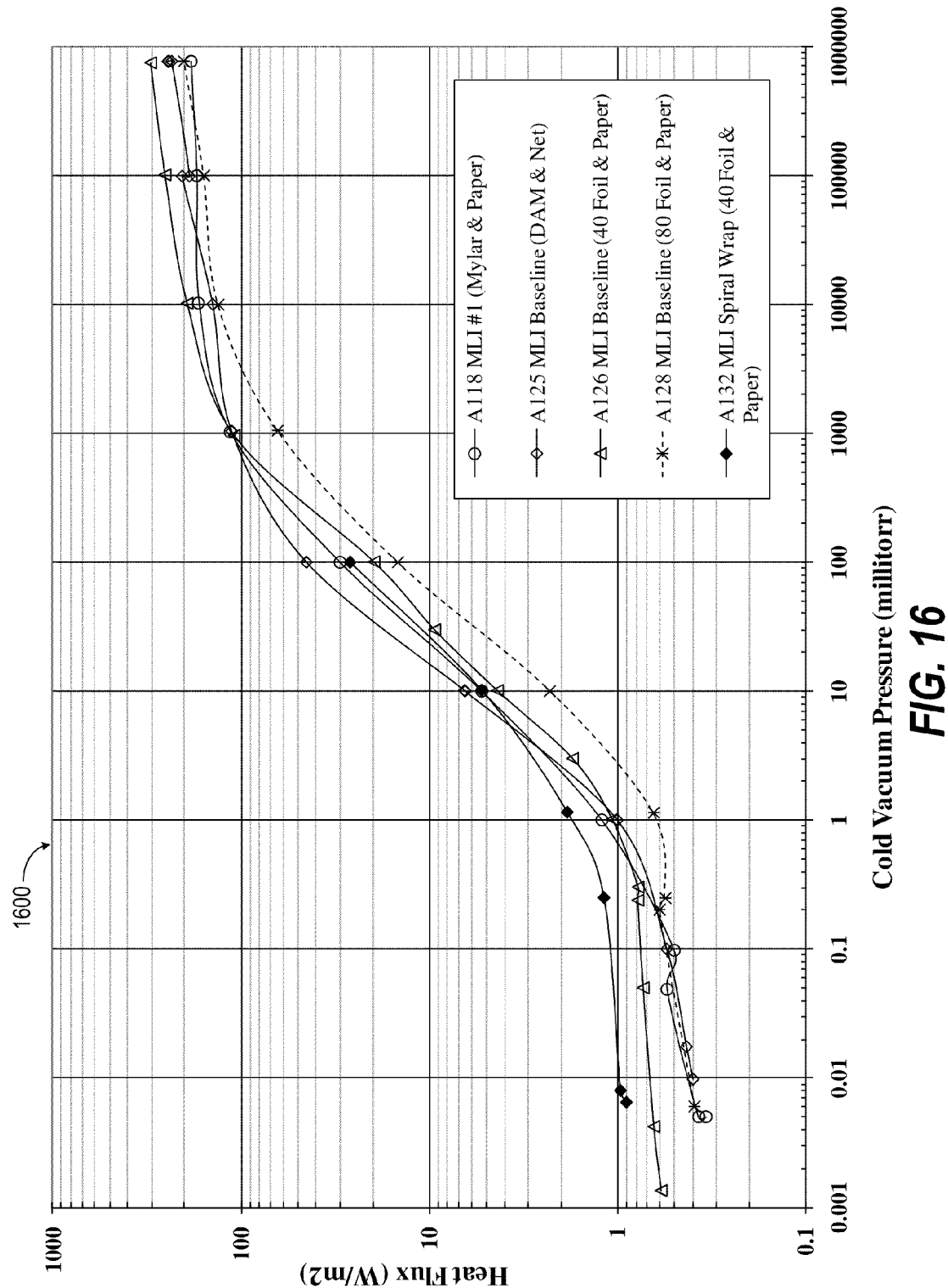
FIG. 16 illustrates a graphical chart for empirical data demonstrating performance for MLI Baseline heat flux.
Figure 17:
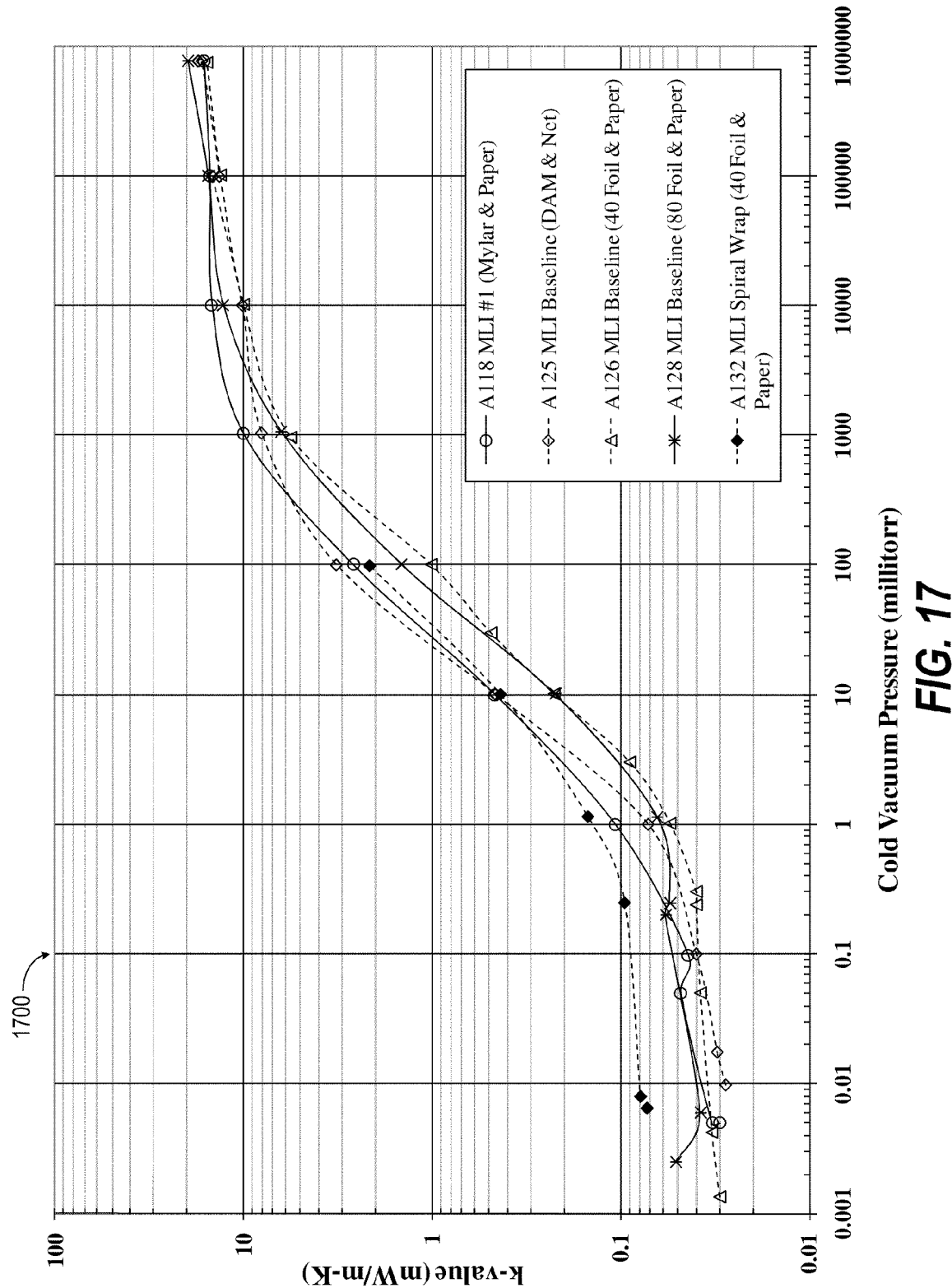
FIG. 17 illustrates a graphical chart for empirical data for MLI.

In FIG. 16, a chart 1600 demonstrates performance by the Cryostat-100 apparatus 100 for MLI Baseline Q provided in k-value. In FIG. 17, a chart 1700 provides the same results in heat flux values. Both depictions emphasize that this four (4) orders of magnitude capability is available in one instrument with one single set-up. The specific specimens plotted are provided in TABLE 7.

TABLE 7

| Comp | Specimen | Form | Material |
|---|---|---|---|
| A118 | MLI #1 (Mylar & Paper) | blanket | MLI |
| A125 | MLI Baseline (DAM & Dacron Net) | blanket | MLI |
| A126 | MLI Baseline (40 Foil & Paper) | blanket | MLI |
| A128 | MLI Baseline (80 Foil & Paper) | blanket | MLI |
| A132 | MLI Spiral Wrap (40 Foil & Paper) | blanket | MLI |

The word "exemplary" is used herein to mean serving as an example, instance, or illustration. Any embodiment or design described herein as "exemplary" is not necessarily to be construed as preferred or advantageous over other embodiments or designs.

Various embodiments will be presented in terms of systems that may include a number of components, modules, and the like. It is to be understood and appreciated that the various systems may include additional components, modules, etc. and/or may not include all of the components, modules, etc. discussed in connection with the figures. A combination of these approaches may also be used.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

It should be appreciated that any patent, publication, or other disclosed material, in whole or in part, that is said to be incorporated by reference herein is incorporated herein only to the extent that the incorporated material does not conflict with existing definitions, statements, or other disclosed material set forth in this specification. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosed material set forth herein, will only be incorporated to the extent that no conflict arises between that incorporated material and the existing disclosed.

We claim:

1. An apparatus for use as an evaporation or boil-off flow measuring device for determining thermal performance of a testing material, comprising:
    a cold mass assembly comprising:
        an inner vessel having a top, a bottom, a sidewall defining a testing chamber, and a sidewall for receiving a testing material,
        an upper guard chamber positioned at the top of the inner vessel, and
        a lower guard chamber positioned at the bottom of the inner vessel;
    an outer vacuum chamber enclosing the inner vessel and the testing material;
    a plurality of liquid conduits for receiving a liquid refrigerant having a normal boiling point below ambient temperature and for venting gas, each of the plurality of liquid conduits communicating through the outer vacuum chamber to a respective one of the testing chamber, the upper guard chamber, and the lower guard chamber; and
    a system of heater elements mounted on a sleeve mounted inside the outer vacuum chamber to provide warm temperature control.

2. The apparatus of claim 1, wherein each of the plurality of liquid conduits comprises a pair of elongate feedthroughs on an upper side of each chamber sized to receive a respective filling tube that is concentric to the elongate feedthrough and extending into the respective chamber, the feedthrough and filling tube sized for a sufficient vent path between the filling tube and the conduit.

3. The apparatus of claim 2, wherein each filling tube comprises a plurality of holes sized to balance cold gas spray effect and rate of filling.

4. The apparatus of claim 1, wherein each of the plurality of liquid conduits comprises an elongate feedthrough on an upper side of each chamber sized to receive a respective filling tube that is concentric to the elongate feedthrough and extending into the respective chamber, the feedthrough and filling tube sized for a sufficient vent path.

5. The apparatus of claim 4, wherein the vacuum chamber comprises a top lid that is detachable from an outer vacuum can, each of the elongate feedthroughs comprising an upper portion that passes through the top lid and connected by a connector to a lower portion that is attached to a cold mass assembly comprised of the testing chamber, the upper guard chamber, and the lower guard chamber.

6. The apparatus of claim 5, further comprising a vacuum port and a vacuum instrumentation feedthrough mounted on the vacuum chamber.

7. The apparatus of claim 5, wherein each of the elongate feedthroughs comprises a respective bellows of sufficiently thin-wall construction for low thermal conduction and mechanical compliance, each bellows comprising an upper bellows connection and a lower bellows connection.

8. The apparatus of claim 7, wherein the upper and lower bellows connection is dimensioned to enable full cryogenic temperature and high vacuum pressure compatibility with minimal leakage and enable removal of the cold mass assembly from the top lid.

9. The apparatus of claim 8, wherein the upper and lower bellows connection further comprises a spherical face seal metal-gasketed fittings.

10. The apparatus of claim 5, further comprising a plurality of handling tools attached to the cold mass assembly for manipulating during installation on a horizontal wrapping machine for test article preparations.

11. The apparatus of claim 5, further comprising a lifting mechanism attachable to the top lid for raising the cold mass assembly from the outer vacuum can.

12. The apparatus of claim 11, further comprising a temperature instrumentation feedthrough provided in the top lid for facilitating removal of the cold mass assembly using the lifting mechanism.

13. The apparatus of claim 11, wherein the lifting mechanism further comprises:
    a lifting frame;
    a vertical jack screw supported by the lifting frame; and
    a lift arm assembly that is received for movement on the vertical jack screw.

14. The apparatus of claim 13, further comprising an elevator frame that is attached for vertical movement to the lifting frame and that is attached to the lift arm assembly to form a carriage,
    wherein the lift arm assembly further comprises a pair of breakaway arms proximally, pivotally attached and pinned to the elevator frame for breakaway vertical rotation and distally engageable to the outer vacuum chamber.

15. The apparatus of claim 13, further comprising a bellows that receives for rotation the vertical jack screw.

16. The apparatus of claim 1, further comprising a plurality of threads or wires for suspending the cold mass assembly within the outer vacuum chamber.

17. The apparatus of claim 16, wherein the plurality of threads are aromatic polyamide fiber threads.

18. The apparatus of claim 16, wherein the plurality of threads are stainless steel wire.

19. The apparatus of claim 1, further comprising at least one warm boundary temperature sensor located on the testing material or the inside of the vacuum chamber, with the warm boundary temperature sensor being spaced a given distance from the sidewall of the inner vessel.

20. The apparatus of claim 19, further comprising at least one cold boundary temperature sensor located on the testing material at a location nearest the inner vessel.

21. The apparatus of claim 20, wherein the warm boundary temperature sensor and the cold boundary temperature sensors are selected from a group consisting of thermocouples, resistance temperature detectors, and silicon diodes.

22. The apparatus of claim 1, further comprising at least one temperature sensor feed-through port in the outer vacuum chamber.

23. The apparatus of claim 1, further comprising:
    at least one vacuum port in the outer vacuum chamber; and
    a baffle plate installed over an entrance to the at least one vacuum port.

24. The apparatus of claim 1, wherein the outer vacuum chamber operates in a pressure range between $1\times10^{-6}$ torr to 760 torr, or $1\times10^{-9}$ torr to 1000 torr, or higher.

25. The apparatus of claim 1, further comprising wherein each of the plurality of liquid conduits comprises an elongate feedthrough on an upper side of each chamber sized to receive an insertable filling tube that is concentric to the elongate feedthrough and extending into the respective chamber, the elongate feedthrough and insertable filling tube sized for a sufficient vent path between the filling tube and the conduit, the insertable filling tube comprising a funnel that is exposed outside of the elongate feedthrough for vertical filling.

26. An apparatus for use as an evaporation or boil-off flow measuring device for determining thermal performance of testing material, comprising:
   a cold mass assembly comprising:
      an inner vessel having a top, a bottom, a sidewall defining a testing chamber, and a sidewall for receiving a testing material,
      an upper guard chamber positioned at the top of the inner vessel, and
      a lower guard chamber positioned at the bottom of the inner vessel;
   an outer vacuum chamber comprising an outer vacuum can sized to enclose the cold mass assembly and the testing material and comprising a top lid that is detachable from the outer vacuum can and comprising at least one lifting support;
   a plurality of elongate feedthroughs for receiving a liquid refrigerant having a normal boiling point below ambient temperature and for venting gas, each of the plurality of elongate feedthroughs communicating through the outer vacuum chamber to a respective one of the testing chamber, the upper guard chamber, and the lower guard chamber, each of the elongate feedthroughs comprising an upper portion that passes through the top lid and connected by a connector to a lower portion that is attached to the cold mass assembly comprised of the testing chamber, the upper guard chamber, and the lower guard chamber; and
   suspension strings attaching the cold mass assembly to an underside of the top lid;
   wherein detaching the top lid from the outer vacuum can allows lifting of the cold mass assembly and the plurality of elongated feedthroughs at the at least one lifting support to install the testing material, and
   wherein the outer vacuum can further comprises a sleeve support and guide positioned to support a lower surface of the cold mass assembly.

27. The apparatus of claim 24, further comprising a lifting mechanism attachable to the top lid for raising the cold mass assembly, rotating the cold mass assembly over the outer vacuum chamber, and lowering cold mass assembly into the outer vacuum can.

28. The apparatus of claim 27, wherein the lifting mechanism is laterally rotatable.

29. The apparatus of claim 28, further comprising a turntable that supports the lifting mechanism for lateral rotation.

* * * * *